(12) United States Patent
Hirano et al.

(10) Patent No.: US 8,362,170 B2
(45) Date of Patent: Jan. 29, 2013

(54) POLYMERIZABLE COMPOUND AND POLYMER COMPOUND OBTAINED BY USING THE SAME

(75) Inventors: Shuji Hirano, Shizuoka (JP); Kaoru Iwato, Shizuoka (JP); Hiroshi Saegusa, Shizuoka (JP); Yusuke Iizuka, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/525,583

(22) Filed: Jun. 18, 2012

(65) Prior Publication Data

US 2012/0271021 A1 Oct. 25, 2012

Related U.S. Application Data

(62) Division of application No. 12/635,998, filed on Dec. 11, 2009.

(30) Foreign Application Priority Data

Dec. 12, 2008 (JP) ................................. 2008-317753

(51) Int. Cl.
*C08F 24/00* (2006.01)

(52) U.S. Cl. ........ 526/270; 526/266; 526/268; 526/280; 526/284; 526/291; 526/328; 526/325.8; 526/332; 526/333; 528/354; 528/361; 528/365; 528/403; 528/425; 549/264; 549/265; 549/298; 549/330; 549/432; 549/433; 549/457; 549/458

(58) Field of Classification Search .................. 526/266, 526/268, 270, 280, 284, 291, 328, 328.5, 526/332, 333; 528/354, 361, 365, 403, 425; 549/264, 265, 298, 330, 432, 433, 457, 458
See application file for complete search history.

(56) References Cited

U.S. PATENT DOCUMENTS

| | | | |
|---|---|---|---|
| 2005/0287473 A1 | 12/2005 | Kodama | |
| 2006/0008736 A1 | 1/2006 | Kanda et al. | |
| 2006/0292490 A1 | 12/2006 | Kodama et al. | |
| 2007/0178405 A1 | 8/2007 | Kanda et al. | |
| 2012/0015301 A1* | 1/2012 | Yoshidome et al. | ........ 430/285.1 |
| 2012/0156617 A1* | 6/2012 | Kataoka et al. | ............ 430/283.1 |

FOREIGN PATENT DOCUMENTS

| | | | |
|---|---|---|---|
| EP | 1612602 A2 | | 1/2006 |
| EP | 1754999 A2 | | 2/2007 |
| JP | 2006-146143 A | | 6/2006 |
| JP | 2006-189713 A | | 7/2006 |
| JP | 2006-276444 A | | 10/2006 |
| JP | 2008-074805 A | | 4/2008 |
| JP | 2010250074 A | * | 11/2010 |
| JP | 2011053360 A | * | 3/2011 |

OTHER PUBLICATIONS

Partial European Search Report issued in Application No: 09178831. 5-1226, dated Mar. 29, 2010.
Extended European Search Report issued May 19, 2010, in counterpart European Application No. 09178831.5.
Communication dated Feb. 21, 2011, issued in corresponding European Patent Application No. 10195102.8.

* cited by examiner

*Primary Examiner* — Richard A Huhn
(74) *Attorney, Agent, or Firm* — Sughrue Mion, PLLC

(57) ABSTRACT

Provided is a polymerizable compound represented by the following general formula (ca-1) or (cb-1):

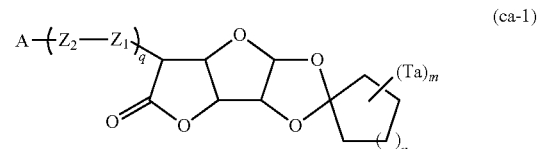

(ca-1)

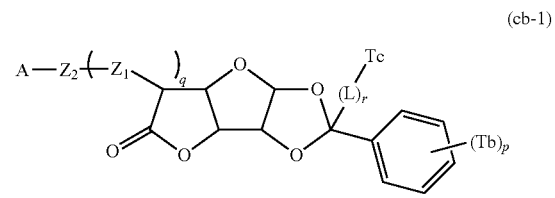

(cb-1)

wherein the variables in the formulae are defined in the specification.

8 Claims, No Drawings

POLYMERIZABLE COMPOUND AND POLYMER COMPOUND OBTAINED BY USING THE SAME

CROSS REFERENCE TO RELATED APPLICATIONS

This is a Divisional Application of U.S. patent application Ser. No. 12/635,998, filed Dec. 11, 2009 which claims priority from Japanese Patent Application No. 2008-317753, filed Dec. 12, 2008, the disclosures of which are incorporated herein by reference.

BACKGROUND OF THE INVENTION

1. Field of the Invention

The present invention relates to a novel polymerizable compound which is useful for optical materials such as optical fibers and optical waveguides, optical disc substrates and photoresists and raw materials thereof, pharmaceutical or agricultural intermediates and raw materials of polymer compounds to be used for other various industrial products and so on and to a polymer compound obtained by using the same. Also, the invention relates to a novel polymerizable compound which is useful for raw materials of polymer compounds to be used for chemical amplification type resist materials for KrF, ArF or $F_2$ excimer lasers, chemical amplification type resist materials for ArF liquid immersion exposure and chemical amplification type resist materials for X-rays, electron beams or EUV (extreme ultraviolet rays) and to a polymer compound obtained by using the same.

2. Description of the Related Art

In chemical amplification resists, an acid is generated in an exposed area upon irradiation with radial rays such as far ultraviolet rays, and the solubility in a developing solution is changed between an exposed area and an unexposed area with active radial rays due to a reaction using this acid as a catalyst, thereby forming a pattern on a substrate.

In the case where a KrF excimer laser is used as an exposure light source, resins having poly(hydroxystyrene) as a basic skeleton, which are low in absorption chiefly in a region of 248 nm, are used as a main component, and therefore, they form a good pattern with a high sensitivity at a high resolution and become a good system as compared with related-art naphthoquinonediazide/novolak resin systems.

On the other hand, in the case where a light source with a shorter wavelength, for example, an ArF excimer laser (193 nm) is used as an exposure light source, compounds having an aromatic group display large absorption essentially in a region of 193 nm, and therefore, they were not sufficient even in the foregoing chemical amplification system. For that reason, resists for ArF excimer laser containing a resin having an alicyclic hydrocarbon structure are being developed.

Furthermore, it has been found that by incorporating a repeating unit having a lactone structure into the foregoing resin having an alicyclic hydrocarbon structure, the performance is enhanced. For example, JP-A-2006-146143 discloses a resin composition using a resin containing a repeating unit having an alicyclic lactone structure.

However, from the viewpoint of overall performance as a resist, it is the actual situation that it is extremely difficult to find out an appropriate combination of a resin, a photoacid generator, an additive, a solvent, etc. to be used. Furthermore, in forming a fine pattern with a line width of not more than 100 nm, improvements in not only a resolving power but also line edge roughness performance of line pattern were demanded.

The "line edge roughness" as referred to herein means that an edge of a resist at an interface between a line pattern and a substrate assumes a shape in which it irregularly fluctuates in a direction vertical to a line direction due to characteristics of the resist. When this pattern is observed from the top, the edge is seen unevenly (from about ± several nm to several ten nm). Such unevenness is transferred onto the substrate in an etching step, and therefore, when the unevenness is large, failure in electrical characteristics is caused, resulting in a lowering in the yield. However, this repeating unit having a lactone structure was problematic in an affinity with a developing solution.

SUMMARY OF THE INVENTION

An object of the invention is to provide a novel polymerizable compound and a novel polymer compound obtained by using the same.

In order to solve the foregoing problems, the present inventor made extensive and intensive investigations, resulting in attaining the following inventions.

(1) A polymerizable compound represented by the following general formula (ca-1) or (cb-1):

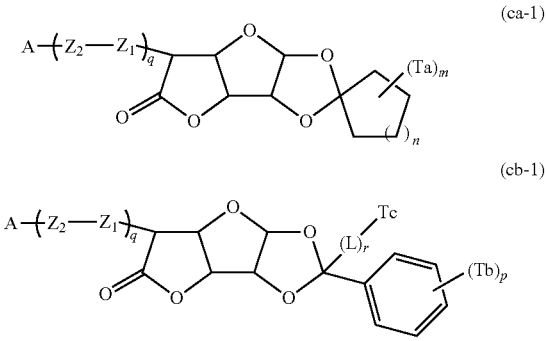

In the foregoing general formulae (ca-1) and (cb-1),

A represents an optionally substituted methacryl group, an optionally substituted acryl group or an optionally substituted norbornene group;

each $Z_1$ independently represents a single bond, an ether bond, an ester bond, an amide bond, a urethane bond or a urea bond;

each $Z_2$ independently represents a single bond or an optionally substituted chain or cyclic alkylene group;

each of Ta and Tb independently represents a halogen atom, an optionally substituted alkyl group, an optionally substituted cycloalkyl group, an optionally substituted alkoxy group, an optionally substituted acyl group, an optionally substituted alkyloxycarbonyl group, a carboxy group, a nitrile group, a hydroxyl group, an optionally substituted amide group or an optionally substituted aryl group; and when plural Tas are present, Tas may be bonded to each other to form a ring; and when plural Tbs are present, Tbs may be bonded to each other to form a fused ring, which may contain a hetero atom, together with the benzene ring on which Tb is substituted.

Tc represents a hydrogen atom, a halogen atom, an optionally substituted alkyl group, an optionally substituted cycloalkyl group, a nitrile group, a hydroxyl group, an optionally substituted amide group or an optionally substituted aryl group;

each L independently represents a carbonyl group, a carbonyloxy group or an ether bond;
m represents an integer of from 1 to 28;
n represents an integer of from 0 to 11;
p represents an integer of from 0 to 5;
q represents an integer of from 0 to 5; and
r represents an integer of from 0 to 5.

(2) The polymerizable compound according as set forth in (1), which is represented by the following general formula (ca-2) or (cb-2):

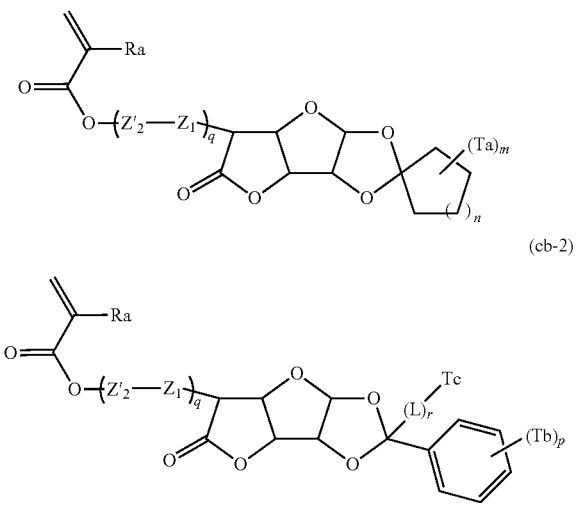

In the foregoing general formulae (ca-2) and (cb-2),
Ra represents a hydrogen atom, a fluorine atom, a methyl group a trifluoromethyl group;
each $Z_1$ independently represents a single bond, an ether bond, an ester bond, an amide bond, a urethane bond or a urea bond;
each $Z_2'$ independently represents an optionally substituted chain or cyclic alkylene group;
each of Ta and Tb independently represents a halogen atom, an optionally substituted alkyl group, an optionally substituted cycloalkyl group, an optionally substituted alkoxy group, an optionally substituted acyl group, an optionally substituted alkyloxycarbonyl group, a carboxy group, a nitrile group, a hydroxyl group, an optionally substituted amide group or an optionally substituted aryl group; and when plural Tas are present, Tas may be bonded to each other to form a ring; and when plural Tbs are present, Tbs may be bonded to each other to form a fused ring, which may contain a hetero atom, together with the benzene ring on which Tb is substituted.
Tc represents a hydrogen atom, a halogen atom, an optionally substituted alkyl group, an optionally substituted cycloalkyl group, a nitrile group, a hydroxyl group, an optionally substituted amide group or an optionally substituted aryl group;
each L independently represents a carbonyl group, a carbonyloxy group or an ether bond;
m represents an integer of from 1 to 28;
n represents an integer of from 0 to 11;
p represents an integer of from 0 to 5;
q represents an integer of from 0 to 5; and
r represents an integer of from 0 to 5.

(3) The polymerizable compound as set forth in (1) or (2), which is represented by the following general formula (ca-3) or (cb-3):

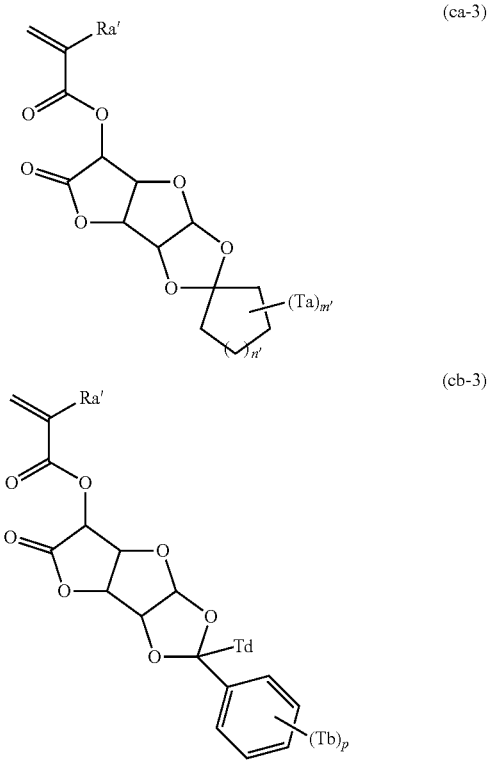

In the foregoing general formulae (ca-3) and (cb-3),
Ra' represents a hydrogen atom or a methyl group;
each of Ta and Tb independently represents a halogen atom, an optionally substituted alkyl group, an optionally substituted cycloalkyl group, an optionally substituted alkoxy group, an optionally substituted acyl group, an optionally substituted alkyloxycarbonyl group, a carboxy group, a nitrile group, a hydroxyl group, an optionally substituted amide group or an optionally substituted aryl group; and when plural Tas are present, Tas may be bonded to each other to form a ring; and when plural Tbs are present, Tbs may be bonded to each other to form a fused ring, which may contain a hetero atom, together with the benzene ring on which Tb is substituted.
Td represents a hydrogen atom or a methyl group;
m' represents an integer of from 1 to 10;
n' represents an integer of from 0 to 2; and
p represents an integer of from 0 to 5.

(4) The polymerizable compound as set forth in (1) or (2), wherein q is 0 or 1.
(5) The polymerizable compound as set forth in any one of (1), (2) and (4), wherein n represents an integer of from 0 to 5, and m represents an integer of from 1 to 10.
(6) The polymerizable compound as set forth in any one of (1), (2), (4) and (5), wherein r is 0 or 1.
(7) The polymerizable compound as set forth in any one of (1), (2) and (4) to (6), wherein $Z_1$ represents an ether bond or an ester bond.
(8) The polymerizable compound as set forth in any one of (1), (2) and (4) to (7), wherein $Z_2$ or $Z_2'$ represents an optionally substituted chain alkylene group.

(9) The polymerizable compound as set forth in (3), wherein n' is 1 or 2.
(10) The polymerizable compound as set forth in (3) or (9), wherein m' is 1 or 2.
(11) A polymer compound obtained by polymerizing the polymerizable compound as set forth in any one of (1) to (10).

The following embodiments are also preferable in the invention.
(12) The polymerizable compound as set forth in any one of (1), (2) and (4) to (8), wherein $Z_1$ represents an ester bond.
(13) The polymerizable compound as set forth in any one of (1), (2), (4) to (8) and (12), wherein the chain alkylene group represented by $Z_2$ or $Z_2'$ is a methylene group, an ethylene group, a propylene group or an isopropylene group.
(14) The polymerizable compound as set forth in any one of (1), (2), (4) to (8), (12) and (13), wherein m is 1 or 2.
(15) The polymerizable compound as set forth in any one of (1), (2), (4) to (8) and (12) to (14), wherein p represents an integer of from 0 to 2.
(16) The polymerizable compound as set forth in any one of (1), (2), (4) to (8) and (12) to (14), wherein p is 5, and all of Tbs are a fluorine atom.
(17) The polymerizable compound as set forth in (3), (9) and (10), wherein p represents an integer of from 0 to 2.
(18) The polymerizable compound as set forth in (3), (9) and (10), wherein p is 5, and all of Tbs are a fluorine atom.

DETAILED DESCRIPTION OF THE INVENTION

The invention is hereunder described in detail.
In the expressions of groups (atomic groups) in this specification, an expression which does not express "substituted" or "unsubstituted" includes both one not having a substituent and one having a substituent. For example, the "alkyl group" includes not only an alkyl group not have a substituent (unsubstituted alkyl group) but an alkyl group having a substituent (substituted alkyl group).

[Polymerizable Compound Represented by the General Formula (ca-1) or (cb-1)]
The polymerizable compound of the invention has a lactone structure, and specifically, it is represented by the following general formula (ca-1) or (cb-1).

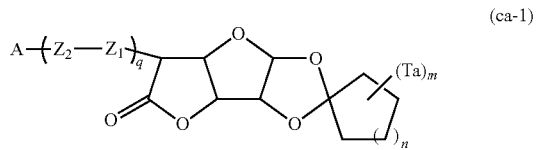
(ca-1)

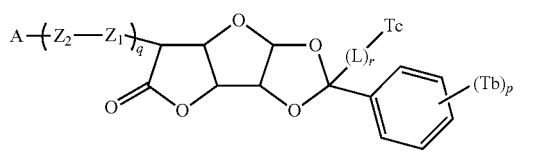
(cb-1)

A represents an optionally substituted methacryl group, an optionally substituted acryl group or an optionally substituted norbornene group. The substituent of the substituted methacryl group, the substituted acryl group or the substituted norbornene group is preferably a halogen atom, and more preferably a fluorine atom. A is preferably an unsubstituted methacryl group, a methacryl group in which a methyl group at the α-position of the carbonyl moiety thereof is replaced by a trifluoromethyl group (α-(trifluoromethyl)acryl group), an unsubstituted acryl group or an acryl group in which a halogen atom at the α-position of the carbonyl moiety thereof is replaced by a fluorine atom (α-fluoroacryl group), and more preferably an unsubstituted methacryl group or an unsubstituted acryl group.

Each $Z_1$ independently represents a single bond, an ether bond (—O—), an ester bond, an amide bond, a urethane bond or a urea bond. $Z_1$ is preferably a single bond, an ether bond or an ester bond, more preferably an ether bond or an ester bond, and further preferably an ester bond.

In the case where the foregoing q is 2 or more, plural groups represented by $Z_1$ may be the same as or different from every other $Z_1$.

Each $Z_2$ independently represents a single bond or an optionally substituted chain or cyclic alkylene group, and preferably an optionally substituted chain or cyclic alkylene group.

The chain alkylene group is preferably a chain alkylene group having from 1 to 10 carbon atoms, more preferably from 1 to 5 carbon atoms, and further preferably from 1 to 3 carbon atoms. Examples thereof include a methylene group, an ethylene group, a propylene group and an isopropylene group.

The cyclic alkylene group is preferably a cyclic alkylene group having from 3 to 20 carbon atoms. Examples thereof include a cyclohexylene group, a cyclopentylene group, a norbornylene group and an adamantylene group.

The group represented by $Z_2$ is more preferably a chain alkylene group.

Each of the chain alkylene group and the cyclic alkylene group is not particularly limited and can have a substituent. Examples of the substituent on each of the chain alkylene group and the cyclic alkylene group include a halogen atom (for example, a fluorine atom, a chlorine atom, a bromine atom, etc.), a mercapto group, a hydroxyl group, an alkoxy group (an alkoxy group having preferably from 1 to 30 carbon atoms, more preferably from 1 to 15 carbon atoms, and further preferably from 1 to 7 carbon atoms; for example, a methoxy group, an ethoxy group, an isopropoxy group, a t-butoxy group, a benzyloxy group, etc.), an alkyl group (a linear or branched alkyl group having preferably from 1 to 30 carbon atoms, more preferably from 1 to 15 carbon atoms, and further preferably from 1 to 6 carbon atoms; for example, a methyl group, an ethyl group, a propyl group, an isopropyl group, a butyl group, a sec-butyl group, a t-butyl group, a pentyl group, a hexyl group, etc.), a cycloalkyl group (a cycloalkyl group having preferably from 3 to 30 carbon atoms, more preferably from 3 to 20 carbon atoms, and further preferably from 3 to 7 carbon atoms; for example, a cyclopropyl group, a cyclobutyl group, a cyclopentyl group, a cyclohexyl group, a cycloheptyl group, etc.), an acyl group (an acyl group having preferably from 2 to 30 carbon atoms, more preferably from 2 to 15 carbon atoms, and further preferably from 2 to 7 carbon atoms; for example, —(C═O)CH$_3$, —(C═O)C$_2$H$_5$, —(C═O)-n-C$_3$H$_7$, —(C═O)-i-C$_3$H$_7$, etc.), an alkyloxycarbonyl group (an alkyloxycarbonyl group having preferably from 2 to 30 carbon atoms, more preferably 2 to 15 carbon atoms, and further preferably from 2 to 7 carbon atoms; for example, —(C═O)OCH$_3$, —(C═O)OC$_2$H$_5$, —(C═O)O-n-C$_3$H$_7$, —(C═O)O-i-C$_3$H$_7$, etc.), a carboxy group, a cyano group, a nitro group, a sulfonyl group, a silyl group, a vinyl group, an aryl group (an aryl group having preferably from 6 to 14 carbon atoms; for example, a phenyl group, a xylyl group, a toluoyl group, a cumenyl group, a naphthyl group, an anthracenyl group, etc.).

In the case where the foregoing q is 2 or more, plural groups represented by $Z_2$ may be the same as or different from every other $Z_2$.

Each of Ta and Tb independently represents a halogen atom, an optionally substituted alkyl group, an optionally substituted cycloalkyl group, an optionally substituted alkoxy group, an optionally substituted acyl group, an optionally substituted alkyloxycarbonyl group, a carboxy group, a nitrile group, a hydroxyl group, an optionally substituted amide group or an optionally substituted aryl group. Of these, a halogen atom, an optionally substituted alkyl group, an optionally substituted cycloalkyl group, an optionally substituted alkoxy group, an optionally substituted alkyloxycarbonyl group and an optionally substituted aryl group are preferable, and a halogen atom, an optionally substituted alkyl group and an optionally substituted alkyloxycarbonyl group are more preferable.

Examples of the halogen atom represented by Ta and Tb include a fluorine atom, a chlorine atom, a bromine atom and an iodine atom. Of these, a fluorine atom is preferable.

As specific examples of the alkyl group, the cycloalkyl group, the alkoxy group, the acyl group and the alkyloxycarbonyl group represented by Ta and Tb, the same groups as the specific examples of the alkyl group, the cycloalkyl group, the alkoxy group, the acyl group and the alkyloxycarbonyl group as the substituent on the chain or cyclic alkylene group as exemplified in the explanation of $Z_2$ can be exemplified.

The aryl group represented by Ta and Tb is preferably an aryl group having from 6 to 14 carbon atoms. Examples thereof include a phenyl group, a xylyl group, a toluoyl group, a cumenyl group, a naphthyl group and an anthracenyl group.

The amide group represented by Ta and Tb is preferably an amide group having from 2 to 7 carbon atoms. Examples thereof include —NH(C=O)CH$_3$, —NH(C=O)C$_2$H$_5$, —NH(C=O)-n-C$_3$H$_7$ and —NH(C=O)-i-C$_3$H$_7$.

Each of the alkyl group, the cycloalkyl group, the alkoxy group, the acyl group, the alkyloxycarbonyl group, the amide group and the aryl group represented by Ta and Tb is not particularly limited and can have a substituent. Specific examples of such a substituent are the same as the specific examples of the substituent on the chain or cyclic alkylene group as exemplified in the explanation of $Z_2$.

When plural Tas are present, Tas may be bonded to each other to form a ring. Example of the ring formed when Tas are bonded to each other include a 5- to 7-membered alicyclic hydrocarbon ring or heterocyclic ring, with a 5- or 6-membered ring being preferable.

When plural Tbs are present, Tbs may be bonded to each other to form a fused ring, which may contain a hetero atom, together with the benzene ring on which Tb is substituted. Examples of the fused ring formed when Tbs are bonded to each other together with the benzene ring include a polycyclic aromatic hydrocarbon. The polycyclic aromatic hydrocarbon preferably has from 10 to 14 carbon atoms, and examples thereof include naphthalene and anthracene.

Tc represents a hydrogen atom, a halogen atom, an optionally substituted alkyl group, an optionally substituted cycloalkyl group, a nitrile group, a hydroxyl group, an optionally substituted amide group or an optionally substituted aryl group.

As the halogen atom, the optionally substituted alkyl group, the optionally substituted cycloalkyl group, the optionally substituted amide group and the optionally substituted aryl group represented by Tc, the same groups as those in Ta and Tb can be exemplified.

The group represented by Tc is preferably a hydrogen atom, a methyl group, an ethyl group, a propyl group or an isopropyl group; more preferably a hydrogen atom, a methyl group or an ethyl group; and most preferably a hydrogen atom or a methyl group.

L represents a carbonyl group, a carbonyloxy group or an ether bond (—O—). In the case where r is an integer of 2 or more, (L)$_r$ represents a group composed of a combination of Ls in the number of r. Plural Ls may be the same as or different from every other L.

m represents an integer of from 1 to 28. m is preferably an integer of from to 10, more preferably an integer of from 1 to 5, and most preferably 1 or 2.

n represents an integer of from 0 to 11. n is preferably an integer of from 0 to 5, more preferably 0, 1 or 2, and most preferably 1 or 2.

p represents an integer of from 0 to 5. p is preferably an integer of from 0 to 3, more preferably an integer of from 0 to 2, and most preferably 1. However, in the case where all of Tbs are a fluorine atom, p is preferably 5.

q represents an integer of from 0 to 5. q is preferably an integer of from 0 to 2, more preferably an integer of from 0 to 1, and most preferably 0.

r represents an integer of from 0 to 5. r is preferably an integer of from 0 to 2, more preferably an integer of from 0 to 1, and most preferably 0.

In the lactone structure described below in the compound represented by the general formula (ca-1) or (cb-1), in general, optical isomers are present, and any optical isomer is useful. Also, one kind of an optical isomer may be used singly, or a mixture of plural optical isomers may be used. In the case of one kind of an optical isomer, its optical purity (ee) is preferably 90% or more, more preferably 95% or more, and most preferably 98% or more.

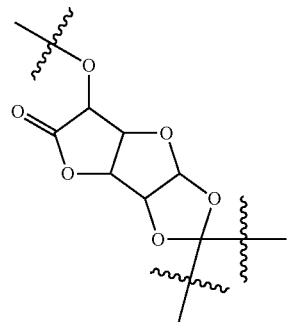 [SMILES: *OC1C(=O)OC2C3OC(*)(*)OC3OC12]

Specific examples of the foregoing stereostructure will be given below, but it should not be construed that the invention is limited thereto.

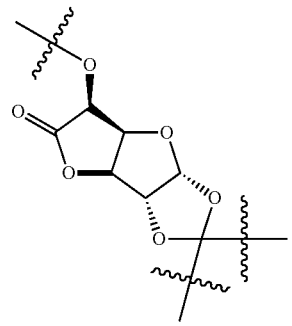

(i)

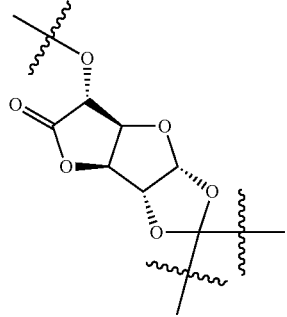

(ii)

(iii)
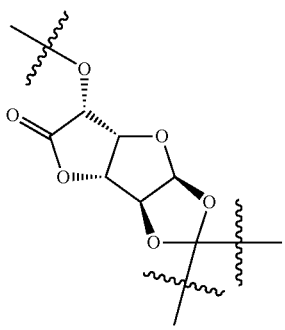

(iv)
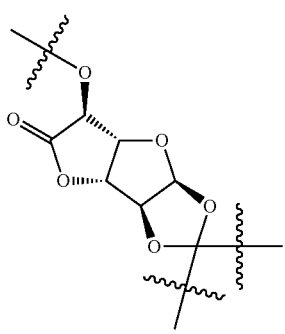

A raw material (starting raw material in the following synthesis routes) which will become the stereostructure represented by the formula (i) is present as a natural product, and it is inexpensively and easily available; and the stereostructure represented by the formula (ii) can be obtained by steric inversion of the stereostructure represented by the formula (i). A raw material which will become the stereostructure represented by the formula (iii) can be synthesized from L-glucose; and the stereostructure represented by the formula (iv) can be obtained by steric inversion of the stereostructure represented by the formula (iii).

In the case where the compound represented by the general formula (ca-1) or (cb-1) is one kind of an optical isomer, it is preferably an optical isomer having the stereostructure represented by the formula (i).

Though a synthesis method of the compound represented by the general formula (ca-1) or (cb-1) is not particularly limited, for example, the compound can be synthesized by the following synthesis routes (the cases where A represents $CH_2=C(Ra)-COO-$ (wherein Ra represents a hydrogen atom, a fluorine atom, a methyl group or a trifluoromethyl group), q is 0, and r is 0 are shown as representative examples).

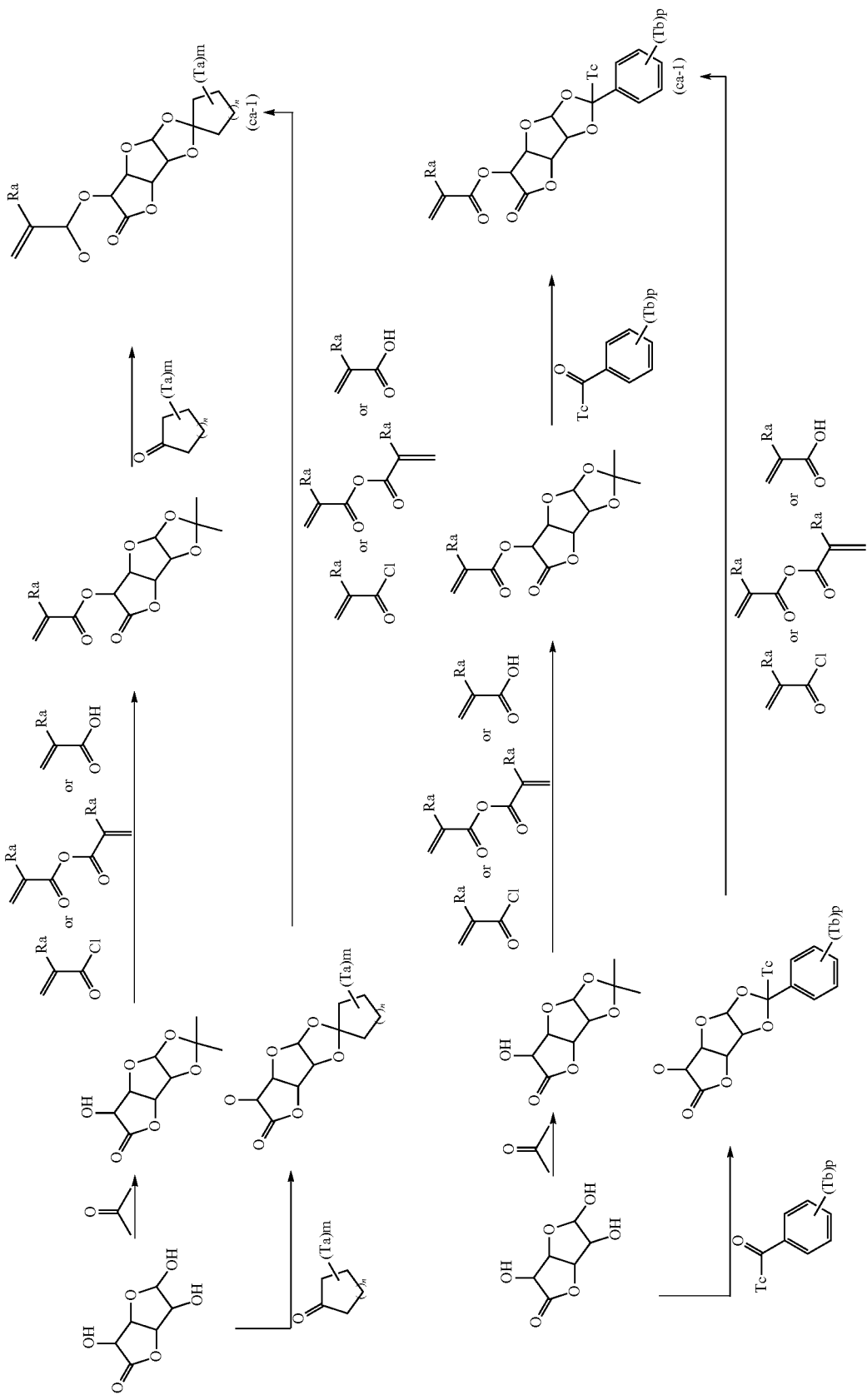

The polymerizable compound represented by the general formula (ca-1) or (cb-1) is preferably represented by the following general formula (ca-2) or (cb-2).

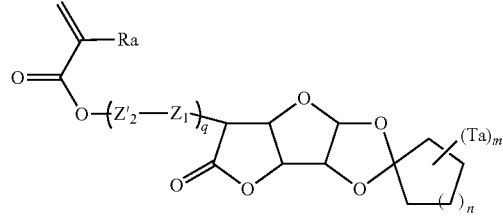
(ca-2)

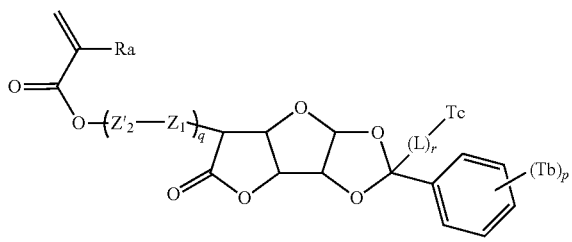
(cb-2)

In the foregoing general formulae (ca-2) and (cb-2),

Ra represents a hydrogen atom, a fluorine atom, a methyl group or a trifluoromethyl group. Ra is preferably a hydrogen atom or a methyl group.

$Z_1$, Ta, Tb, Tc, L, m, n, p, q and r are respectively synonymous with $Z_1$, Ta, Tb, Tc, L, m, n, p, q and r in the general formula (ca-1) or (cb-1); and preferred examples thereof are also the same.

Each $Z_2'$ independently represents an optionally substituted chain or cyclic alkylene group. Preferred examples and specific examples thereof are synonymous with those of the optionally substituted chain or cyclic alkylene group represented by $Z_2$ in the general formula (ca-1) or (cb-1).

The polymerizable compound represented by the general formula (ca-1) or (cb-1) is more preferably represented by the following general formula (ca-3) or (cb-3).

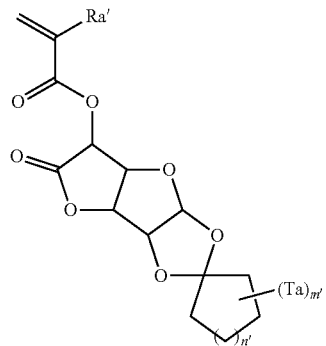
(ca-3)

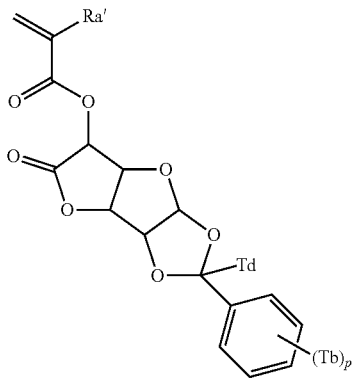
(cb-3)

In the foregoing general formulae (ca-3) and (cb-3),

Ra' represents a hydrogen atom or a methyl group.

Ta and Tb are respectively synonymous with Ta and Tb in the general formula (ca-1) or (cb-1); and preferred examples thereof are also the same.

Td represents a hydrogen atom or a methyl group.

m' represents an integer of from 1 to 10. m' is preferably an integer of from 1 to 5, and more preferably 1 or 2.

n' represents an integer of from 0 to 2. n' is preferably 1 or 2.

p represents an integer of from 0 to 5. p is preferably an integer of from 0 to 3, more preferably an integer of from 0 to 2, and most preferably 1. However, in the case where all of Tbs are a fluorine atom, p is preferably 5.

Specific examples of the polymerizable compound of the invention will be given below, but it should not be construed that the invention is limited thereto.

In the following chemical formulae, Ra represents a hydrogen atom, a fluorine atom, a methyl group or a trifluoromethyl group; and Td represents a hydrogen atom or a methyl group.

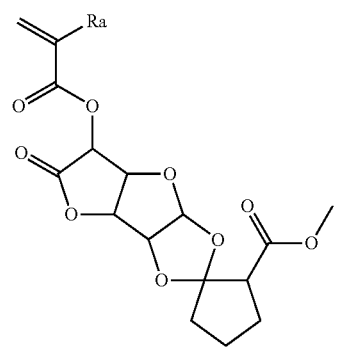

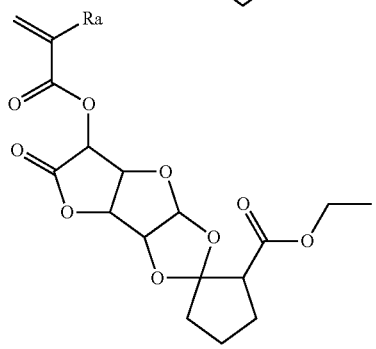

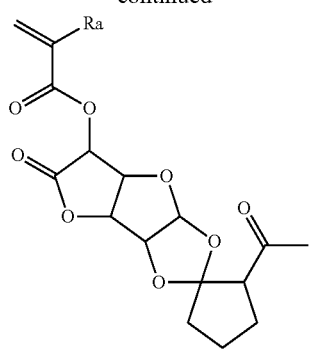
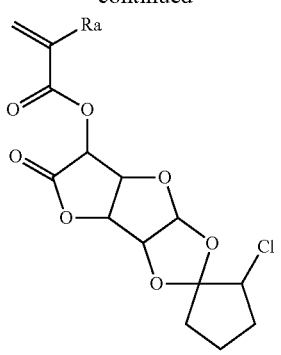
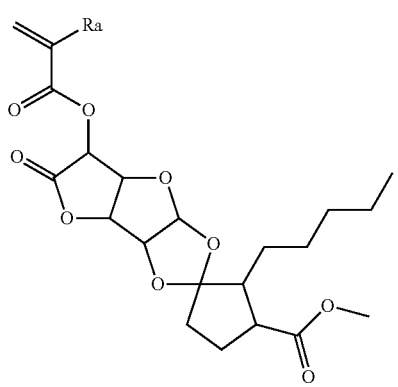
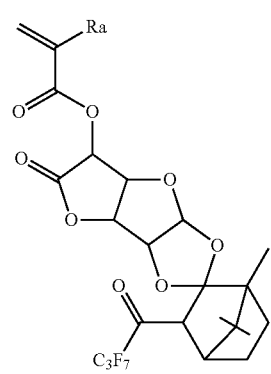
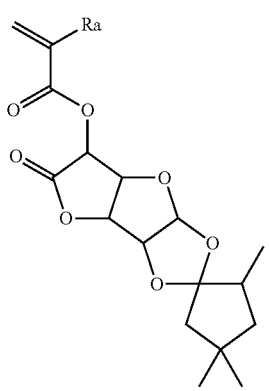
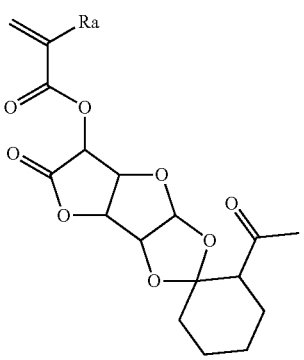
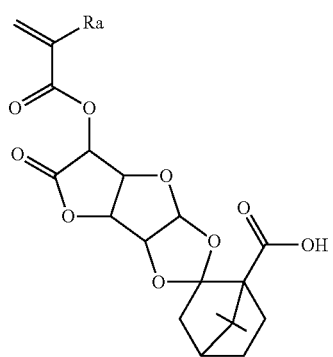
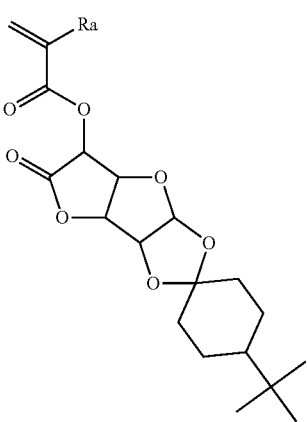

-continued
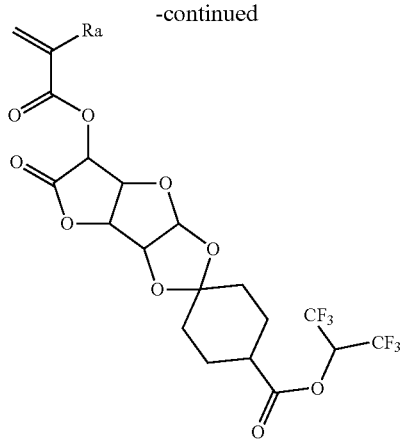
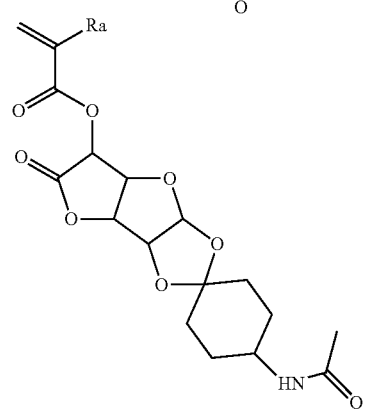
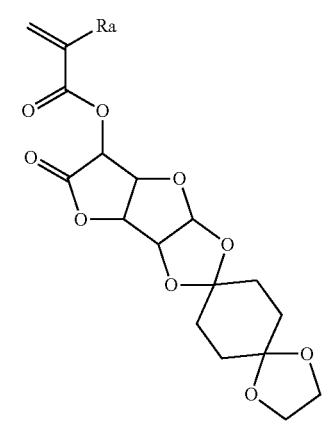
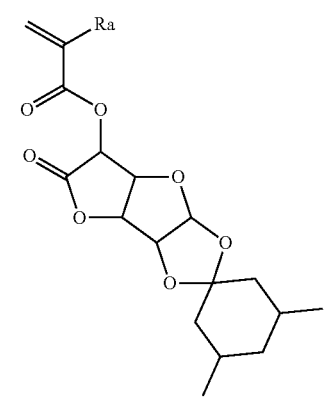
-continued
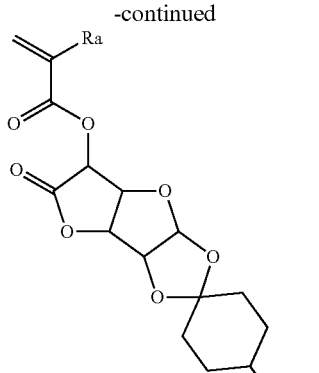
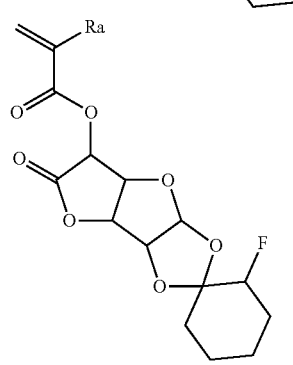
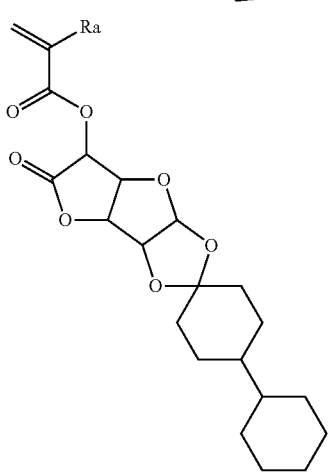
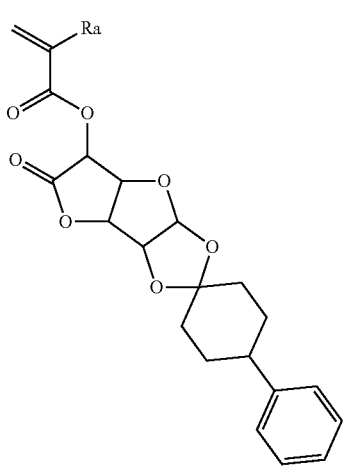

-continued
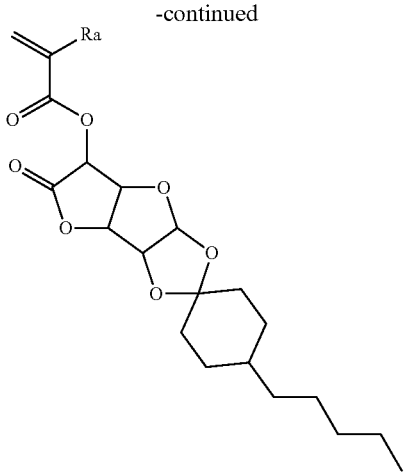
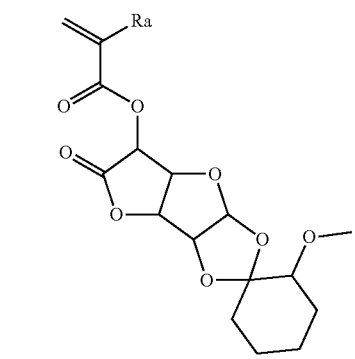
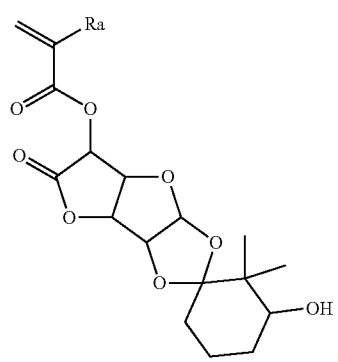
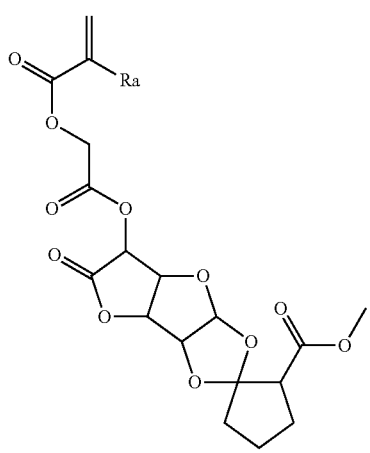
-continued
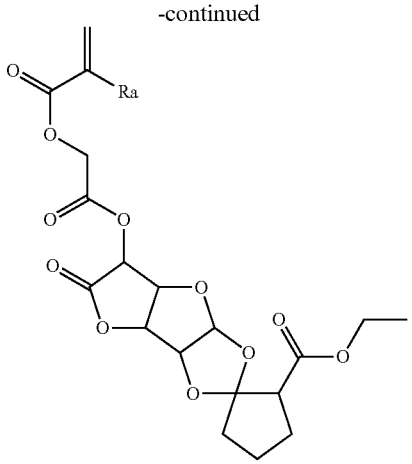
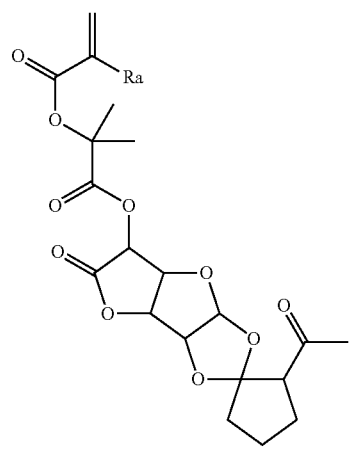
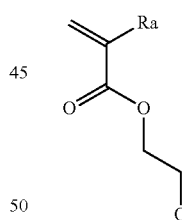
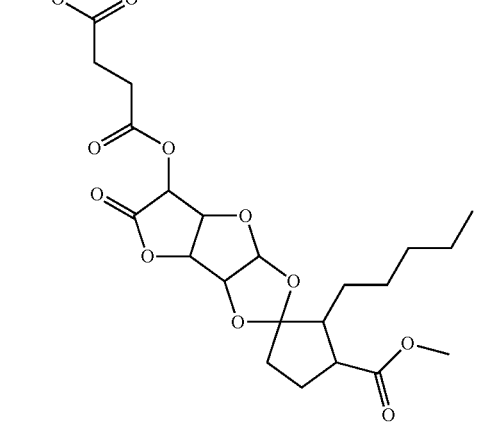

-continued
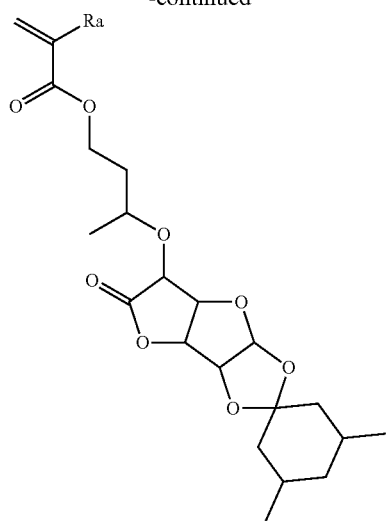
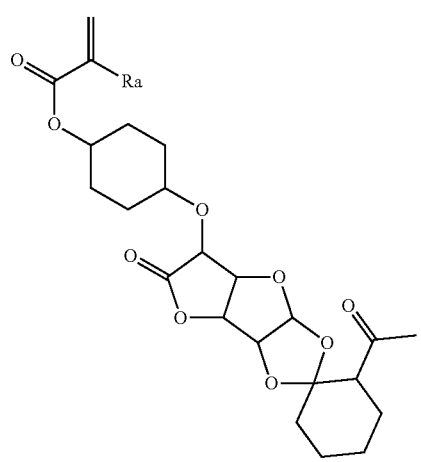
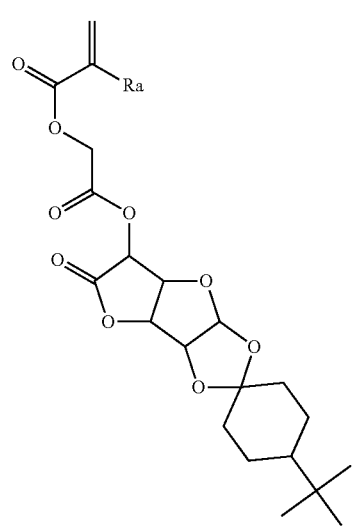
-continued
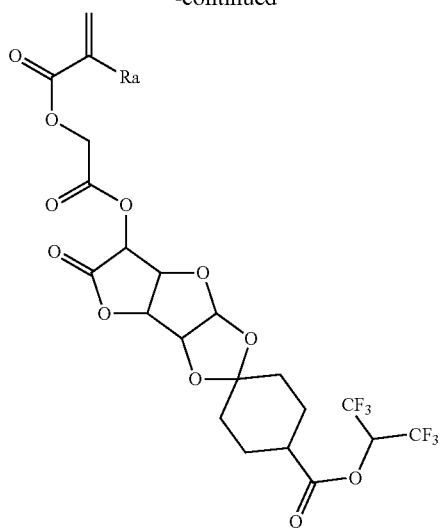
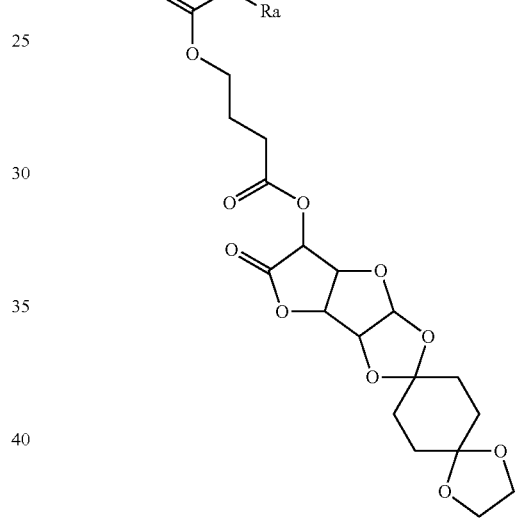
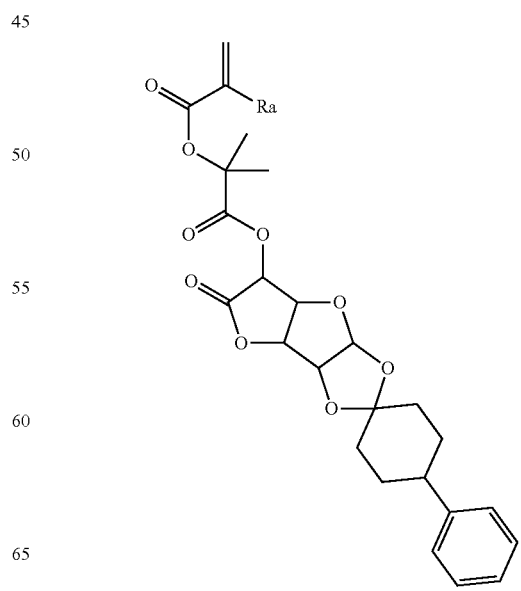

23
-continued
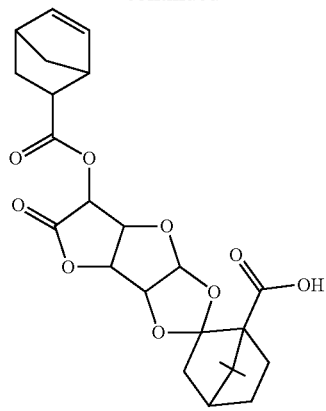
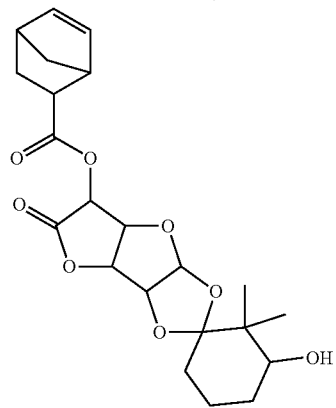
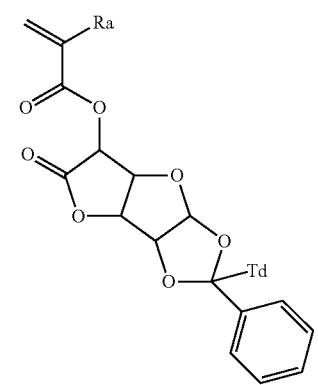
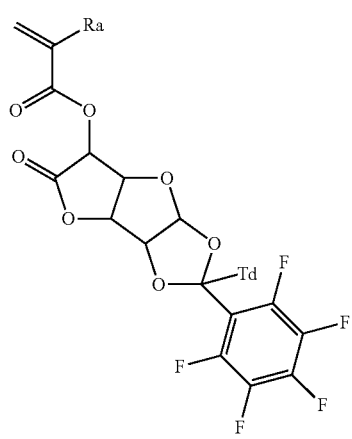
24
-continued
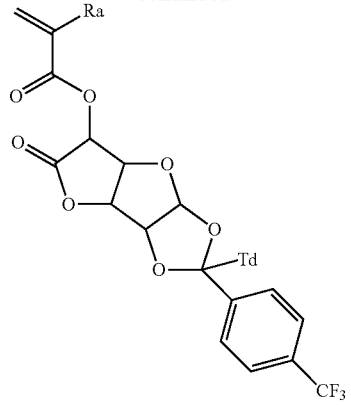
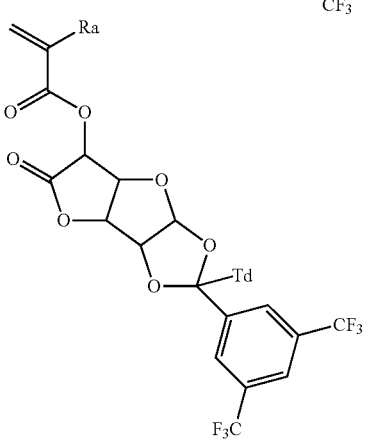
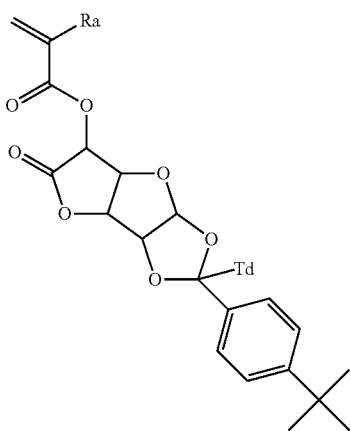
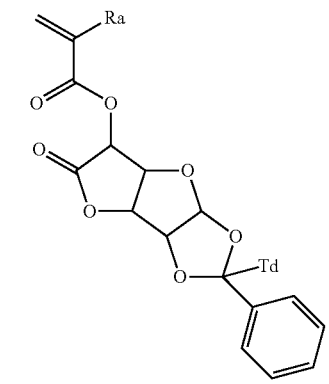

-continued
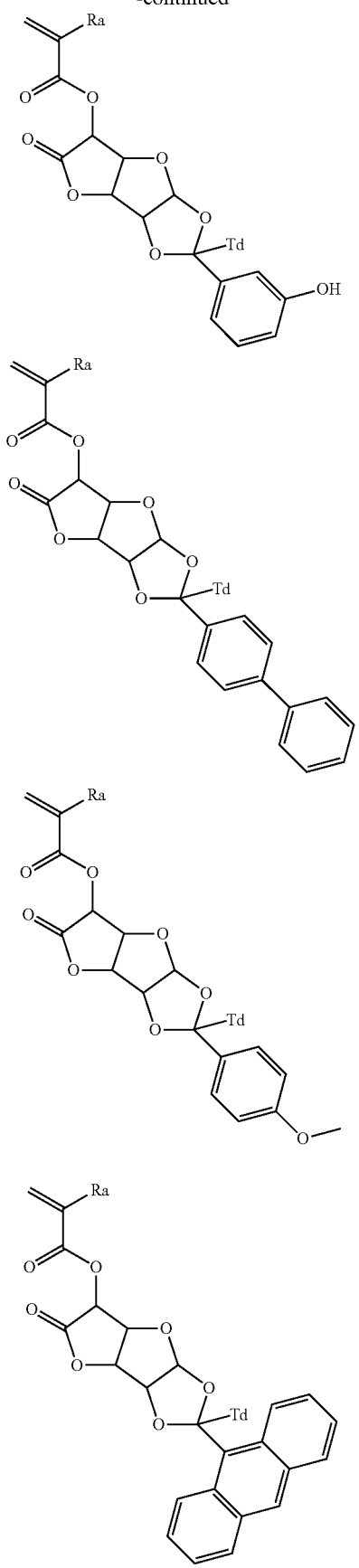
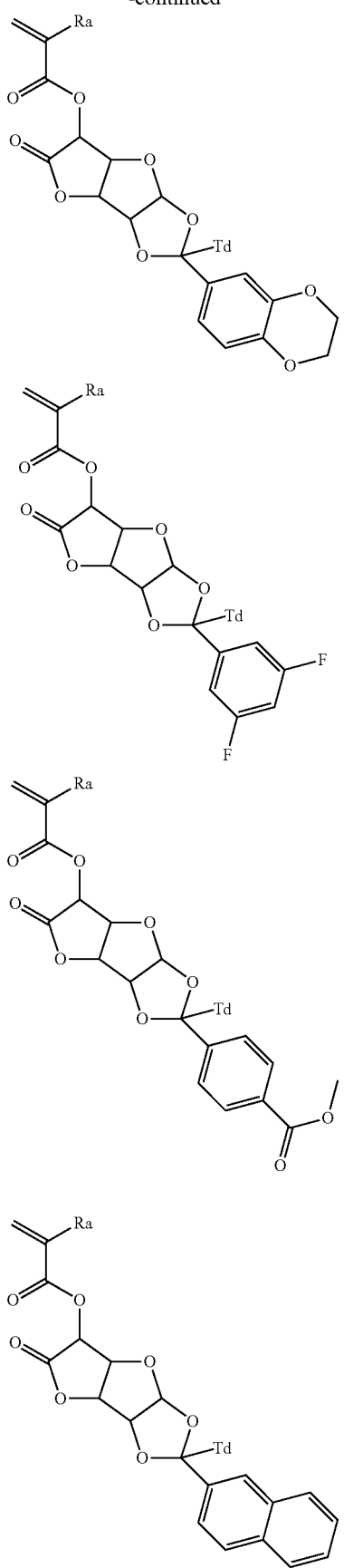

27
-continued
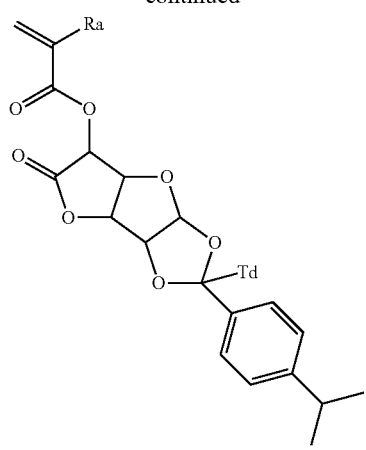
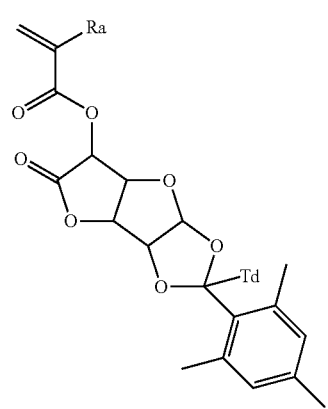
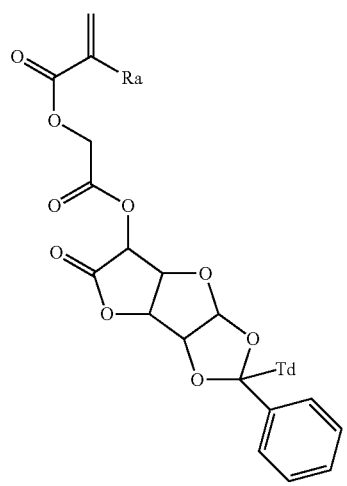
28
-continued
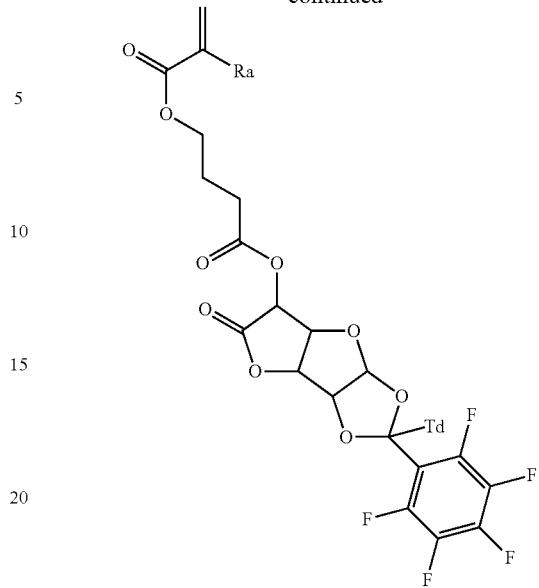
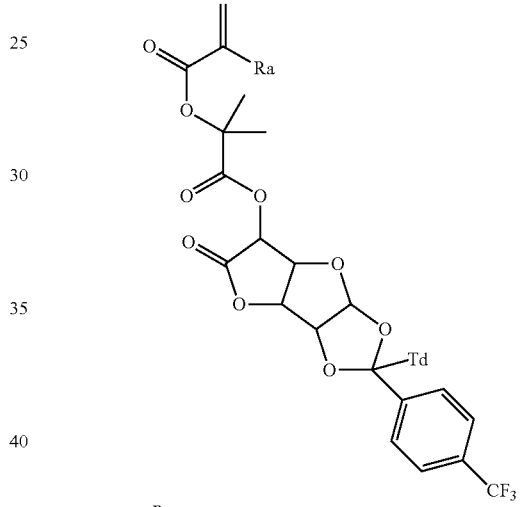
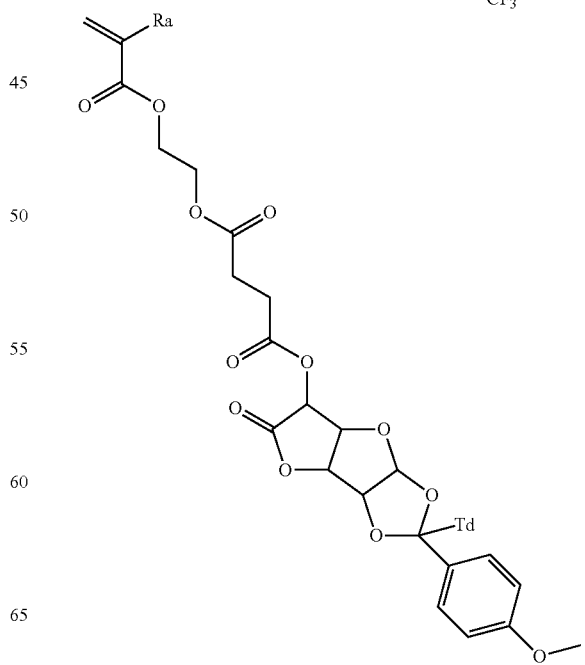

29
-continued
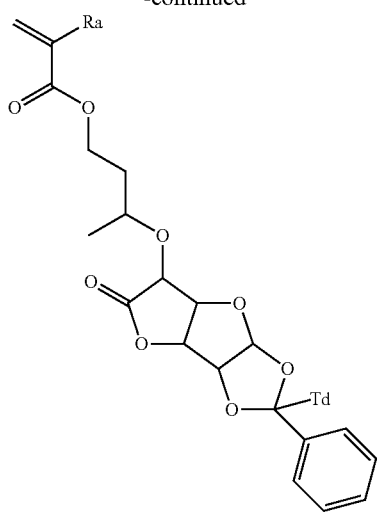
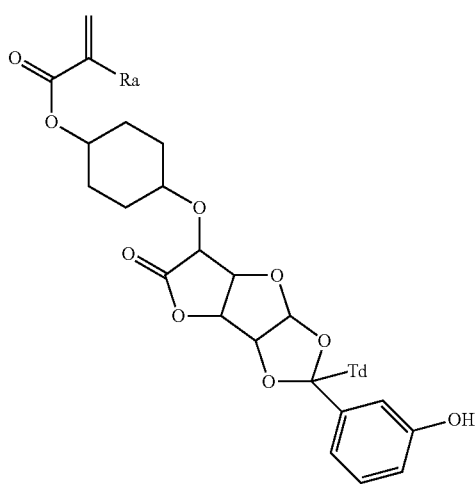
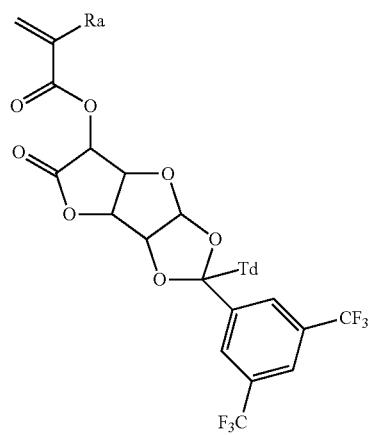
30
-continued
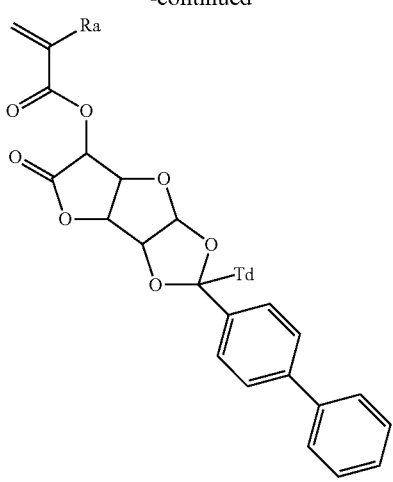
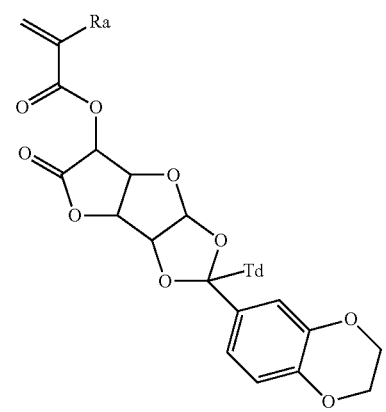
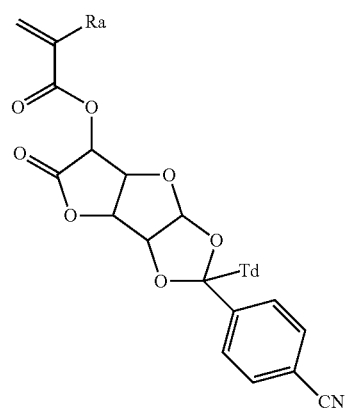

31
-continued

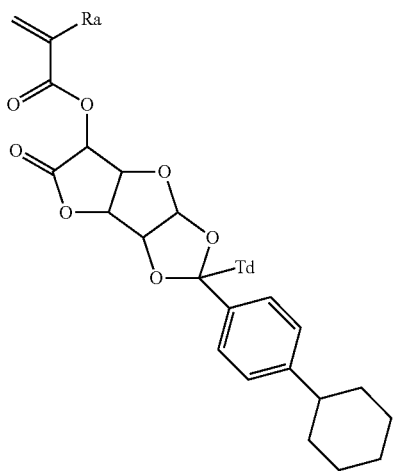

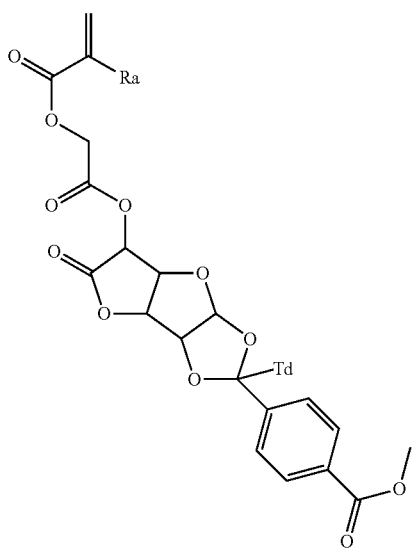

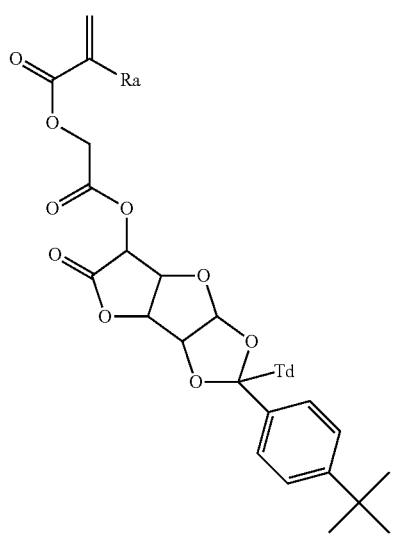

32
-continued

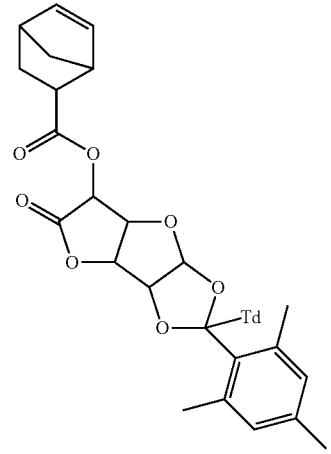

[Polymer Compound Having a Repeating Unit Corresponding to the Polymerizable Compound Represented by the General Formula (ca-1) or (cb-1)]

The polymer compound having a repeating unit corresponding to the polymerizable compound represented by the general formula (ca-1) or (cb-1) is obtained by polymerizing one or more of the polymerizable compound represented by the general formula (ca-1) or (cb-1).

The polymer compound of the invention may properly have other repeating unit in addition to the repeating unit corresponding to the polymerizable compound represented by the general formula (ca-1) or (cb-1). In that case, the amount of the repeating unit corresponding to the polymerizable compound represented by the general formula (ca-1) or (cb-1) is, for example, from 1 to 100% by mole, preferably from 3 to 100% by mole, more preferably from 5 to 100% by mole, and most preferably from 10 to 100% by mole relative to the whole of the repeating units of the polymer compound.

The polymer compound having a repeating unit corresponding to the polymerizable compound of the invention can be synthesized according to the usual way (for example, radical polymerization). Examples of a general synthesis method include a batch polymerization method in which a monomer species (the polymerizable compound represented by the general formula (ca-1) or (cb-1) and a comonomer which is used, if desired) and an initiator are dissolved in a solvent, and the solution is heated for polymerization; and a dropping polymerization method in which a solution of a monomer species and an initiator is added dropwise to a heated solvent over from 1 to 10 hours. Of these, a dropping polymerization method is preferable. Examples of the reaction solvent include ethers such as tetrahydrofuran, 1,4-dioxane and diisopropyl ether; ketones such as methyl ethyl ketone and methyl isobutyl ketone; ester solvents such as ethyl acetate; amide solvents such as dimethylformamide and dimethylacetamide; and solvent capable of dissolving therein the polymer compound of the invention as described later, such as propylene glycol monomethyl ether acetate, propylene glycol monomethyl ether and cyclohexanone.

The polymerization reaction is preferably carried out in an inert gas atmosphere such as nitrogen and argon. As to the polymerization initiator, the polymerization is started using a commercially available radical initiator (for example, an azo based initiator, a peroxide, etc.). The radical initiator is preferably an azo based initiator; and an azo based initiator having an ester group, a cyano group or a carboxyl group is preferable. Examples of the preferred initiator include azobisisobutyronitrile, azobisdimethylvaleronitrile and dimethyl 2,2'-azobis(2-methylpropionate). If desired, the initiator is supplemented or added dividedly; and after completion of the reaction, the reaction mixture is thrown into a solvent, and a desired polymer is recovered by a method such as powder or solid recovery. The concentration of the reaction solution is from 5 to 50% by mass, preferably from 10 to 50% by mass, and more preferably from 15 to 50% by mass. The reaction temperature is usually from 10° C. to 150° C., preferably from 30° C. to 120° C., and more preferably from 60° C. to 100° C.

After completion of the reaction, the reaction mixture is allowed to stand for cooling to room temperature and then purified. For the purification, a usual method such as a liquid-liquid extraction method in which the purification is carried out by removing a residual monomer and an oligomer component by washing with water or through a combination with an appropriate solvent; a purification method in which the purification is carried out in a solution state by means of ultrafiltration for extracting and removing only materials having a molecular weight of a specified value or less; a reprecipitation method in which the purification is carried out by adding dropwise a resin solution to a poor solvent to solidify the resin in the poor solvent, thereby removing a residual monomer or the like; a purification method in which the purification is carried out in a solid state by washing a filtered resin slurry with a poor solvent or other means can be applied. For example, the foregoing resin is deposited as a solid by bringing the reaction solution into contact with a solvent in which the resin is sparingly soluble or insoluble (poor solvent), in a volume amount of not more than 10 times, and preferably from 10 to 5 times the reaction solution.

As the solvent (precipitation or reprecipitation solvent) which is used in a precipitation or reprecipitation operation from the polymer solution, a poor solvent of the polymer is useful. The poor solvent can be properly selected and used among hydrocarbons, halogenated hydrocarbons, nitro compounds, ethers, ketones, esters, carbonates, alcohols, carboxylic acids, water and mixed solvents containing such a solvent, depending upon the type of the polymer. Of these, a solvent containing at least an alcohol (in particular, methanol, etc.) or water is preferable as the precipitation or reprecipitation solvent.

The use amount of the precipitation or reprecipitation solvent can be properly selected while taking into consideration efficiency, yield and the like. The use amount of the precipitation or reprecipitation solvent is in general from 100 to 10,000 parts by mass, preferably from 200 to 2,000 parts by mass, and more preferably from 300 to 1,000 parts by mass based on 100 parts by mass of the polymer solution.

The temperature for achieving the precipitation or reprecipitation can be properly selected while taking into consideration the efficiency or operability. The temperature for achieving the precipitation or reprecipitation is usually from about 0 to 50° C., and preferably in the vicinity of room temperature (for example, from about 20 to 35° C.). The precipitation or reprecipitation operation can be carried out using a customary mixing container such as a stirring tank by a known method such as a batch type method and a continuous type method.

The precipitated or reprecipitated polymer is usually subjected to customary solid-liquid separation such as filtration and centrifugation, dried and then provided for use. The filtration is carried out using a solvent-resistant filter medium preferably under a pressure. The drying is carried out under an atmospheric pressure or reduced pressure (preferably under a reduced pressure) at a temperature of from about 30 to 100° C., and preferably from about 30 to 50° C.

The resin which has been once deposited and separated may be again dissolved in a solvent and brought into contact with a solvent in which the resin is sparingly soluble or insoluble. That is, there may be adopted a method including a step of after completion of the foregoing radical polymerization reaction, bringing the reaction mixture into contact with a solvent in which the polymer is sparingly soluble or insoluble, thereby depositing the resin (step a); a step of separating the resin from the solution (step b); a step of again dissolving the resin in a solvent, thereby preparing a resin solution A (step c); a step of subsequently bringing a solvent in which the resin is sparingly soluble or insoluble in a volume amount of less than 10 times (preferably a volume amount of not more than 5 times) the resin solution A into contact with the resin solution A, thereby depositing a resin solid (step d); and a step of separating the deposited resin (step e).

A weight average molecular weight of the polymer compound having a repeating unit corresponding to the polymerizable compound of the invention is preferably from 1,000 to 200,000, more preferably from 2,000 to 20,000, further preferably from 3,000 to 15,000, and especially preferably from 3,000 to 10,000 in terms of a reduced value into polystyrene by the GPC method.

A degree of dispersion (molecular weight distribution) of the polymer compound which is used is usually in the range of from 1 to 3, preferably from 1 to 2.6, more preferably from 1 to 2, and especially preferably from 1.4 to 1.7.

The polymer compound having a repeating unit corresponding to the polymerizable compound of the invention has an excellent affinity with an alkaline developing solution, and therefore, for example, when added to a positive working resist composition containing an acid decomposable resin and a compound capable of generating an acid upon irradiation of active rays or radial rays, the developability of a resist film becomes excellent, and a good pattern can be formed.

Also, when the polymer compound having a repeating unit corresponding to the polymerizable compound of the invention further contains an acid decomposable group-containing repeating unit as a comonomer component, an acid decomposable resin having an excellent affinity with an alkaline developing solution can be formed; and therefore, with respect to a resist film obtained by a positive working resist composition containing, in addition to such an acid decomposable resin, for example, a compound capable of generating an acid upon irradiation with active rays or radial rays, its developability becomes excellent, and a good pattern can be formed.

EXAMPLES

The invention is more specifically described below with reference to the following Examples. However, it should be construed that the invention is not limited to these Examples whatever.

Example 1

Synthesis of Compound (c)

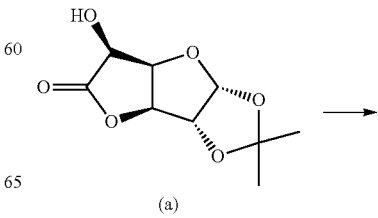

(a)

-continued

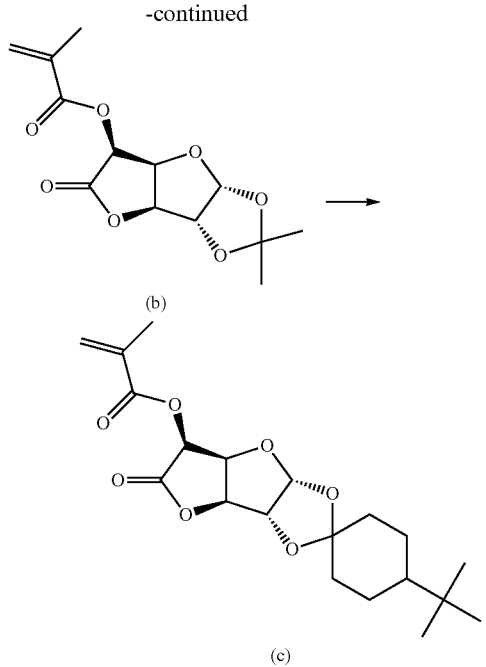

To 200.0 g of 1,2-O-isopropylidene-α-D-glucurono-6,3-lactone (a) (manufactured by Tokyo Chemical Industry Co., Ltd.), one liter of tetrahydrofuran (THF) was added; the mixture was stirred for dissolution; the solution was cooled to 0° C. in a nitrogen atmosphere; and 187.2 of triethylamine was added thereto. Thereafter, 214.6 of methacrylic anhydride was added dropwise, and after completion of the dropwise addition, the mixture was stirred for one hour. The resulting mixture was allowed to stand for cooling at 25° C. and stirred for an additional 4 hours; after confirming disappearance of the raw material (a), 4 L of ethyl acetate was added; the mixture was washed with 1 N hydrochloric acid, sodium hydrogencarbonate and distilled water (two times); and an organic layer was concentrated. A seed crystal of Compound (b) was added to form a powder, which was then recrystallized from hexane/ethyl acetate, thereby obtaining 162.0 g of Compound (b).

30.0 g of the above-obtained Compound (b), 150 mL of toluene, 19.5 g of 4-tert-butylcyclohexanone, 0.3 g of sulfuric acid and 0.3 g of α-methoxyphenol were added; the mixture was stirred in a nitrogen atmosphere at 70° C. for 14 hours; and after confirming disappearance of Compound (b), the reaction mixture was neutralized bu the addition of a sodium hydrogencarbonate powder. 500 mL of ethyl acetate was added, the mixture was washed with 300 mL of distilled water three times, and an organic layer was concentrated. The resulting mixture was isolated and purified by means of column chromatography, thereby obtaining 12.7 of a target material (c).

$^1$H-NMR of Compound (c) (ppm, CDCl$_3$): 0.82 (9H, s), 0.90 to 1.10 (1H, m), 1.18 to 1.50 (4H, m), 1.50 to 1.82 (4H, m), 1.98 (3H, s), 4.86 (1H, d), 4.90 (1H, d), 5.09 (1H, dd), 5.55 (1H, d), 5.68 to 5.76 (1H, m), 6.02 (1H, d), 6.31 (1H, s)

Example 2

Synthesis of Compound (g)

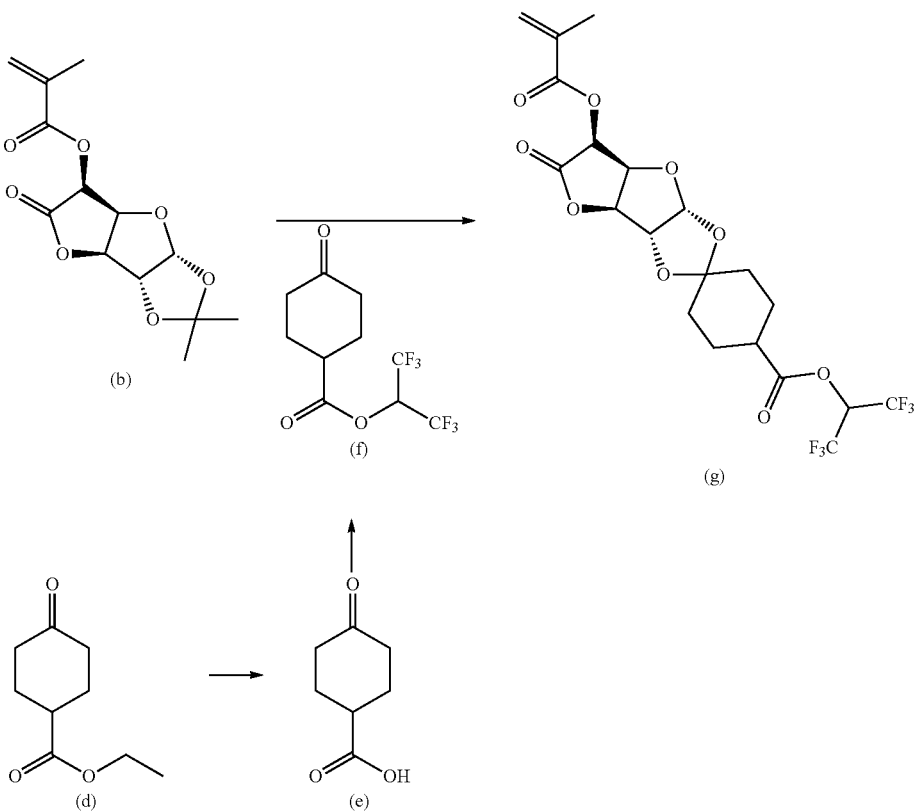

To 150.0 g of ethyl 4-cyclohexanonecarboxylate (d), 300.0 g of methanol was added, the mixture was stirred, and a sodium hydroxide aqueous solution (mixed solution of 35.3 g of sodium hydroxide and 300.0 g of distilled water) was added dropwise thereto at 25° C. After 3 hours, disappearance of Compound (d) was confirmed, and the reaction solution was added dropwise to 45.7 g of concentrated hydrochloric acid. 2,400 g of ethyl acetate was added, the mixture was washed with distilled water 5 times, and an organic layer was concentrated, thereby obtaining 63 g of Compound (e).

43.7 g of the above-obtained Compound (e), 394.0 g of chloroform, 77.6 g of 1,1,1,3,3,3-hexafluoro-2-propanol and 3.8 g of dimethylaminopyridine were added; the mixture was stirred; 64.9 g of 1-ethyl-3-(3-dimethylaminopropyl)carbodiimide hydrochloride was added; the mixture was stirred at 25° C. for 3 hours; and after confirming disappearance of Compound (e), 1 N hydrochloric acid was added dropwise to the reaction solution. After stirring, an organic layer was taken out and washed with 1 N hydrochloric acid two times and with distilled water 5 times, respectively; and an organic layer was concentrated, thereby obtaining 70.0 g of Compound (f).

Using 32.1 g of Compound (f) and 26.0 g of Compound (b), 10.0 g of a target material (g) was obtained in the same manner as in Example 1.

$^1$H-NMR of Compound (g) (ppm, CDCl$_3$): 1.52 to 2.10 (8H, m), 2.00 (3H, s), 2.52 to 2.66 (1H, m), 4.85 (1H, d), 4.93 (1H, d), 5.09 (1H, dd), 5.54 (1H, d), 5.70 to 5.76 (1H, m), 5.70 (1H, sep), 6.04 (1H, d), 6.31 (1H, s)

Example 3

Synthesis of Compound (h)

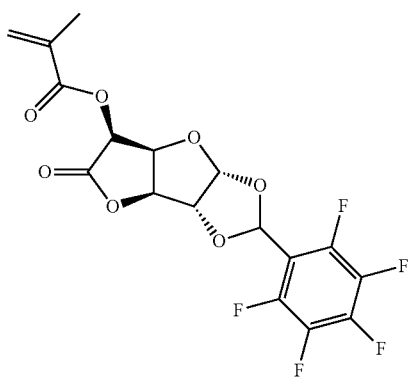

Using 20.7 g of pentafluorobenzaldehyde and 25.0 g of Compound (b), 12.0 g of a target material (h) was obtained in the same manner as in Example 1.

$^1$H-NMR of Compound (h) (ppm, CDCl$_3$): 2.02 (3H, s), 4.93 (1H, d), 5.02 (1H, d), 5.31 (1H, dd), 5.66 (1H, d), 5.70 to 5.78 (1H, m), 6.16 (1H, d), 6.20 (1H, s), 6.32 (1H, s)

Example 4

Synthesis of Compound (i)

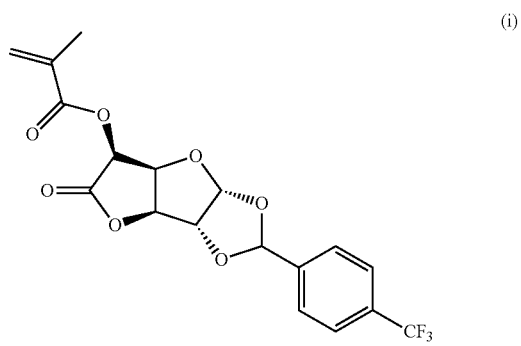

Using 22.1 g of 4-(trifluoromethyl)benzaldehyde and 30.0 g of Compound (b), 13.5 g of a target material (i) was obtained in the same manner as in Example 1.

$^1$H-NMR of Compound (i) (ppm, CDCl$_3$): 2.03 (3H, s), 5.03 (1H, d), 5.10 (1H, d), 5.17 (1H, dd), 5.56 (1H, d), 5.76 (1H, s), 6.07 (1H, s), 6.19 (1H, d), 6.34 (1H, s), 7.56 (2H, d), 7.67 (2H, d)

Example 5

Synthesis of Compound (j)

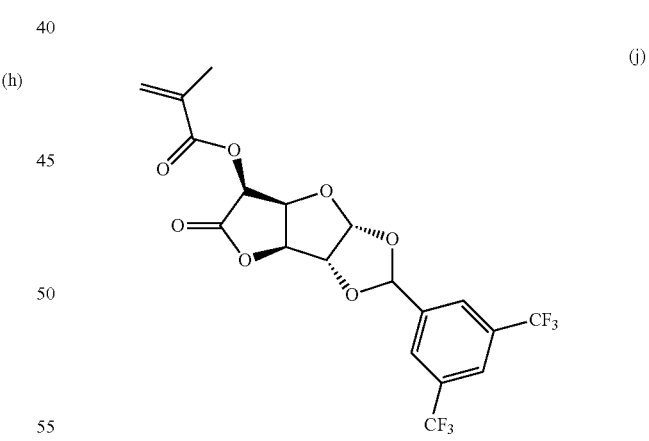

Using 24.5 g of 3,5-bis(trifluoromethyl)benzaldehyde and 24.0 g of Compound (b), 14.0 g of a target material (j) was obtained in the same manner as in Example 1.

$^1$H-NMR of Compound (j) (ppm, CDCl$_3$): 1.98 (3H, s), 4.86 (1H, dd), 4.98 (1H, d), 5.02 (1H, d), 5.54 (1H, d), 5.70 to 5.78 (1H, m), 6.10 (1H, s), 6.24 (1H, d), 6.31 (1H, s), 7.96 (3H, s)

Example 6

Synthesis of Compound (k)

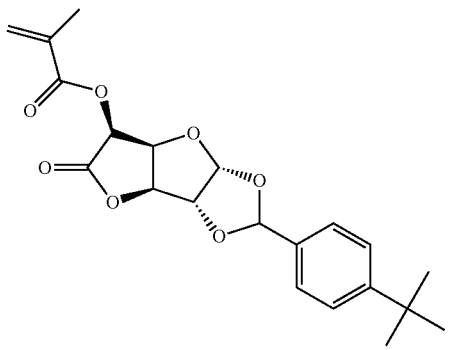

Using 20.6 g of 4-tert-butylbenzaldehyde and 30.0 g of Compound (b), 14.3 g of a target material (k) was obtained in the same manner as in Example 1.

$^1$H-NMR of Compound (k) (ppm, CDCl$_3$): 1.34 (9H, s), 2.20 (3H, s), 5.01 (1H, dd), 5.09 (1H, d), 5.15 (1H, dd), 5.56 (1H, d), 5.70 to 5.80 (1H, m), 6.00 (1H, d), 6.17 (1H, dd), 6.33 (1H, d), 7.30 to 7.50 (4H, m)

Example 7

Synthesis of Polymer (1)

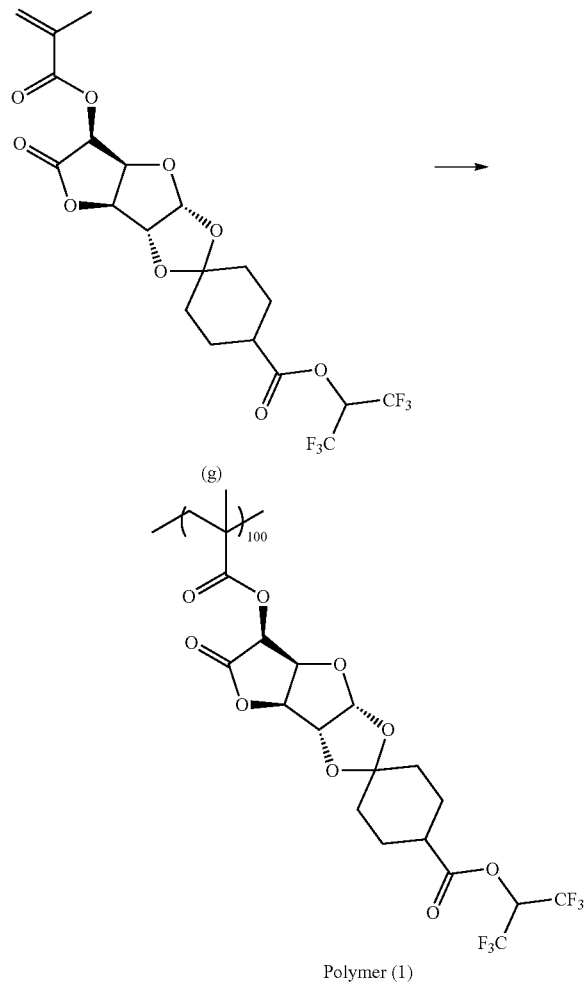

A three-necked flask was charged with 10.1 g of propylene glycol monomethyl ether acetate (PGMEA) in a nitrogen atmosphere and heated at 80° C. A solution having 36.3 g of Compound (g) and a polymerization initiator V-601 (manufactured by Wako Pure Chemical Industries, Ltd.) in an amount of 2.5% by mole relative to the monomer dissolved in 96.8 g of PGMEA was added dropwise thereto over 4 hours. After completion of the dropwise addition, the mixture was allowed to react at 80° C. for an additional 4 hours. The reaction solution was allowed to stand for cooling and then added dropwise to a mixed solution of 1,300 g of methanol and 150 g of distilled water over 20 minutes; and a deposited powder was collected by filtration and dried to obtain 25.1 g of Polymer (1).

The resulting Polymer (1) had a weight average molecular of 13,000 as reduced into standard polystyrene by the GPC method and a degree of dispersion (Mw/Mn) of 1.38.

Example 8

Synthesis of Polymer (2)

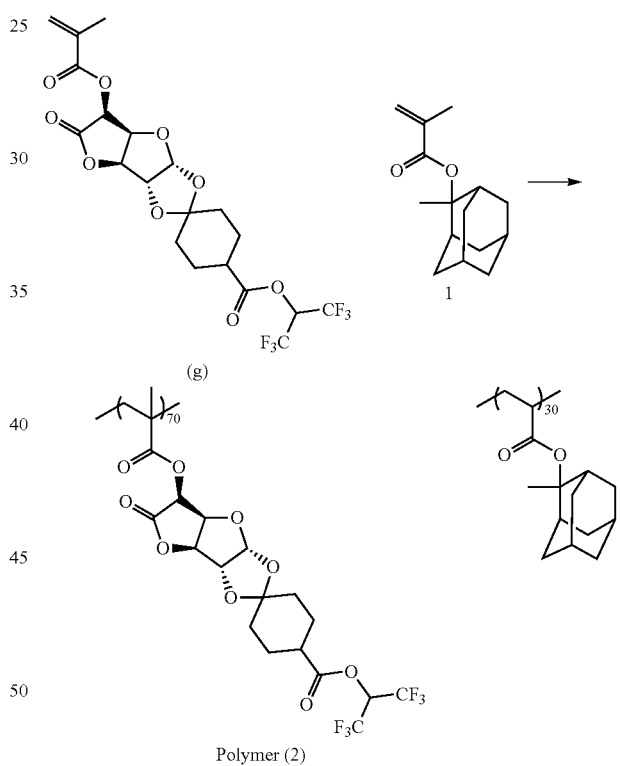

A three-necked flask was charged with 9.0 g of PGMEA in a nitrogen atmosphere and heated at 80° C. A solution having 25.4 g of Compound (g), 4.9 g of Compound (1) and a polymerization initiator V-601 (manufactured by Wako Pure Chemical Industries, Ltd.) in an amount of 7.5% by mole relative to the monomers dissolved in 81.2 g of PGMEA was added dropwise thereto over 4 hours. After completion of the dropwise addition, the mixture was allowed to react at 80° C. for an additional 4 hours. The reaction solution was allowed to stand for cooling and then added dropwise to a mixed solution of 1,080 g of methanol and 120 g of distilled water over 20 minutes; and a deposited powder was collected by filtration and dried to obtain 16.5 g of Polymer (2).

The resulting Polymer (2) had a weight average molecular of 4,000 as reduced into standard polystyrene by the GPC method and a degree of dispersion (Mw/Mn) of 1.42.

Example 9

Synthesis of Polymer (3)

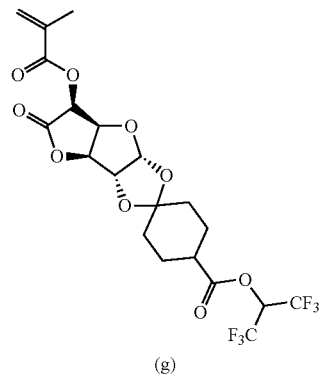
(g)

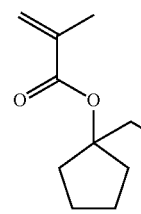
2

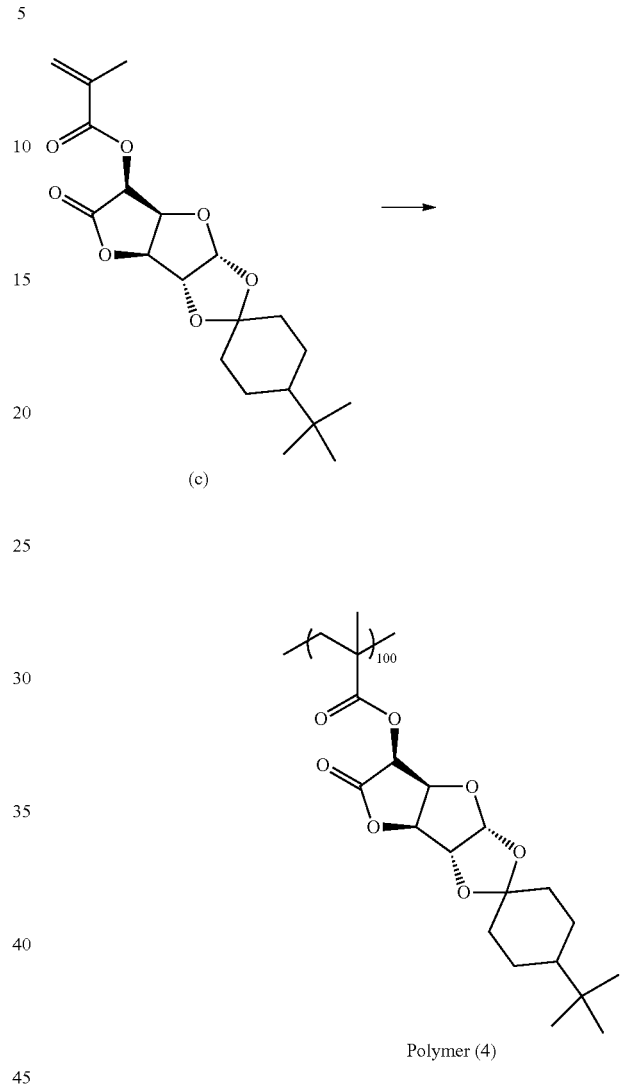

Polymer (3)

A three-necked flask was charged with 10.9 g of PGMEA in a nitrogen atmosphere and heated at 80° C. A solution having 21.8 g of Compound (g), 5.1 g of Compound (2) and a polymerization initiator V-601 (manufactured by Wako Pure Chemical Industries, Ltd.) in an amount of 5.0% by mole relative to the monomers dissolved in 97.6 g of PGMEA was added dropwise thereto over 4 hours. After completion of the dropwise addition, the mixture was allowed to react at 80° C. for an additional 4 hours. The reaction solution was allowed to stand for cooling and then added dropwise to a mixed solution of 1,300 g of methanol and 150 g of distilled water over 20 minutes; and a deposited powder was collected by filtration and dried to obtain 20.2 g of Polymer (3).

The resulting Polymer (3) had a weight average molecular of 8,000 as reduced into standard polystyrene by the GPC method and a degree of dispersion (Mw/Mn) of 1.32.

Example 10

Synthesis of Polymer (4)

(c)

Polymer (4)

A three-necked flask was charged with 91.3 g of PGMEA in a nitrogen atmosphere and heated at 85° C. A solution having 76.1 g of Compound (c) and a polymerization initiator V-601 (manufactured by Wako Pure Chemical Industries, Ltd.) in an amount of 3.0% by mole relative to the monomer dissolved in 137.0 g of PGMEA was added dropwise thereto over 4 hours. After completion of the dropwise addition, the mixture was allowed to react at 85° C. for an additional 4 hours. The reaction solution was allowed to stand for cooling and then added dropwise to a mixed solution of 2,700 g of methanol and 300 g of distilled water over 20 minutes; and a deposited powder was collected by filtration and dried to obtain 53.3 g of Polymer (4).

The resulting Polymer (4) had a weight average molecular of 3,800 as reduced into standard polystyrene by the GPC method and a degree of dispersion (Mw/Mn) of 1.29.

Example 11

Synthesis of Polymer (5)

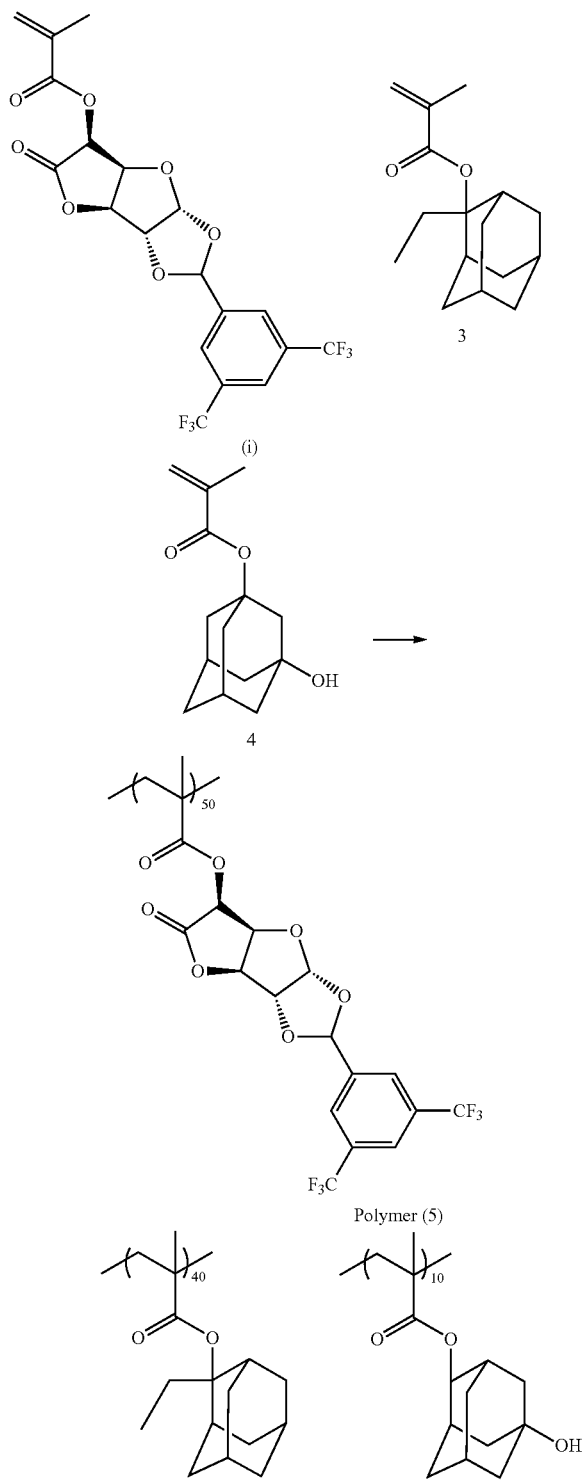

A three-necked flask was charged with 85.7 g of PGMEA in a nitrogen atmosphere and heated at 85° C. A solution having 46.8 g of Compound (j), 19.9 g of Compound (3), 4.7 g of Compound (4), 3.6 g of 1-dodecanethiol and a polymerization initiator V-601 (manufactured by Wako Pure Chemical Industries, Ltd.) in an amount of 3.0% by mole relative to the monomers dissolved in 200.0 g of PGMEA was added dropwise thereto over 4 hours. After completion of the dropwise addition, the mixture was allowed to react at 85° C. for an additional 4 hours. The reaction solution was allowed to stand for cooling and then added dropwise to a mixed solution of 2,000 g of methanol and 220 g of distilled water over 20 minutes; and a deposited powder was collected by filtration and dried to obtain 57.1 g of Polymer (5).

The resulting Polymer (5) had a weight average molecular of 4,100 as reduced into standard polystyrene by the GPC method and a degree of dispersion (Mw/Mn) of 1.26.

Example 12

Synthesis of Polymer (6)

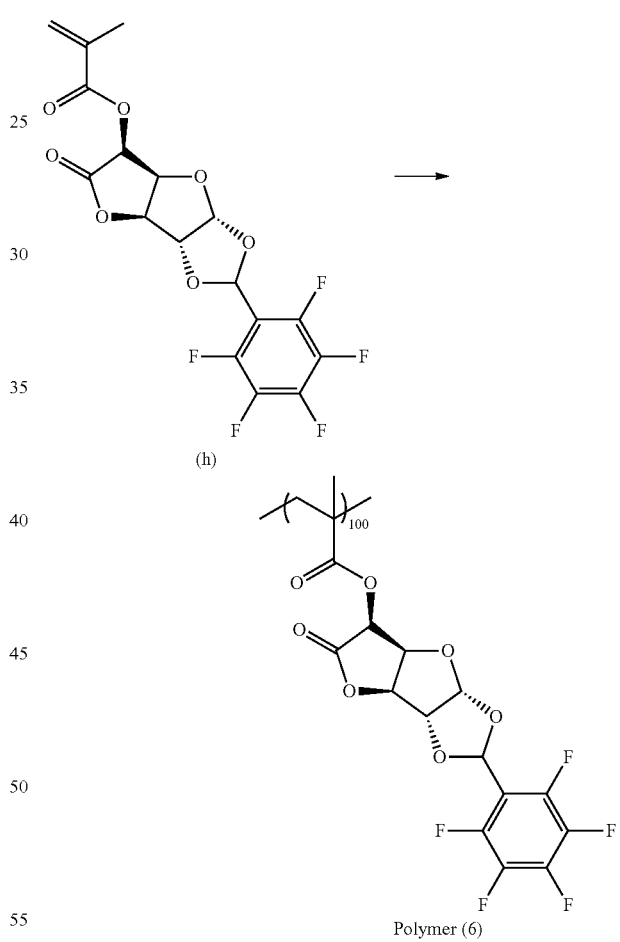

A three-necked flask was charged with 76.0 g of PGMEA in a nitrogen atmosphere and heated at 85° C. A solution having 63.3 g of Compound (h) and a polymerization initiator V-601 (manufactured by Wako Pure Chemical Industries, Ltd.) in an amount of 4.0% by mole relative to the monomer dissolved in 177.3 g of PGMEA was added dropwise thereto over 4 hours. After completion of the dropwise addition, the mixture was allowed to react at 85° C. for an additional 4 hours. The reaction solution was allowed to stand for cooling and then added dropwise to a mixed solution of 1,800 g of methanol and 200 g of distilled water over 20 minutes; and a deposited powder was collected by filtration and dried to obtain 44.3 g of Polymer (6).

The resulting Polymer (6) had a weight average molecular of 6,300 as reduced into standard polystyrene by the GPC method and a degree of dispersion (Mw/Mn) of 1.35.

Example 13

Synthesis of Polymer (7)

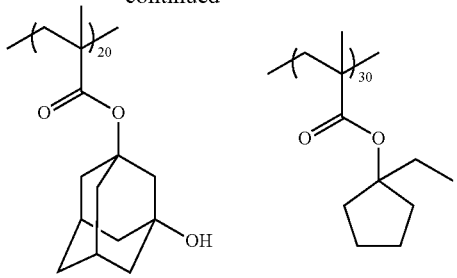

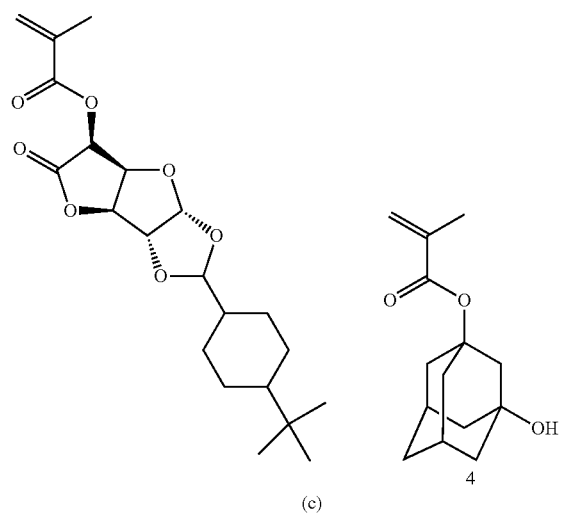

A three-necked flask was charged with 62.8 g of cyclohexanone in a nitrogen atmosphere and heated at 80° C. A solution having 29.6 g of Compound (c), 7.1 g of Compound (4), 8.2 g of Compound (2) and a polymerization initiator AIBN (manufactured by Wako Pure Chemical Industries, Ltd.) in an amount of 7.0% by mole relative to the monomers dissolved in 116.7 g of cyclohexanone was added dropwise thereto over 6 hours. After completion of the dropwise addition, the mixture was allowed to react at 80° C. for an additional 2 hours. The reaction solution was allowed to stand for cooling and then added dropwise to a mixed solution of 1,100 g of heptane and 450 g of ethyl acetate over 20 minutes; and a deposited powder was collected by filtration and dried to obtain 33.7 g of Polymer (7).

The resulting Polymer (7) had a weight average molecular of 7,800 as reduced into standard polystyrene by the GPC method and a degree of dispersion (Mw/Mn) of 1.46.

Example 14

Synthesis of Polymer (8)

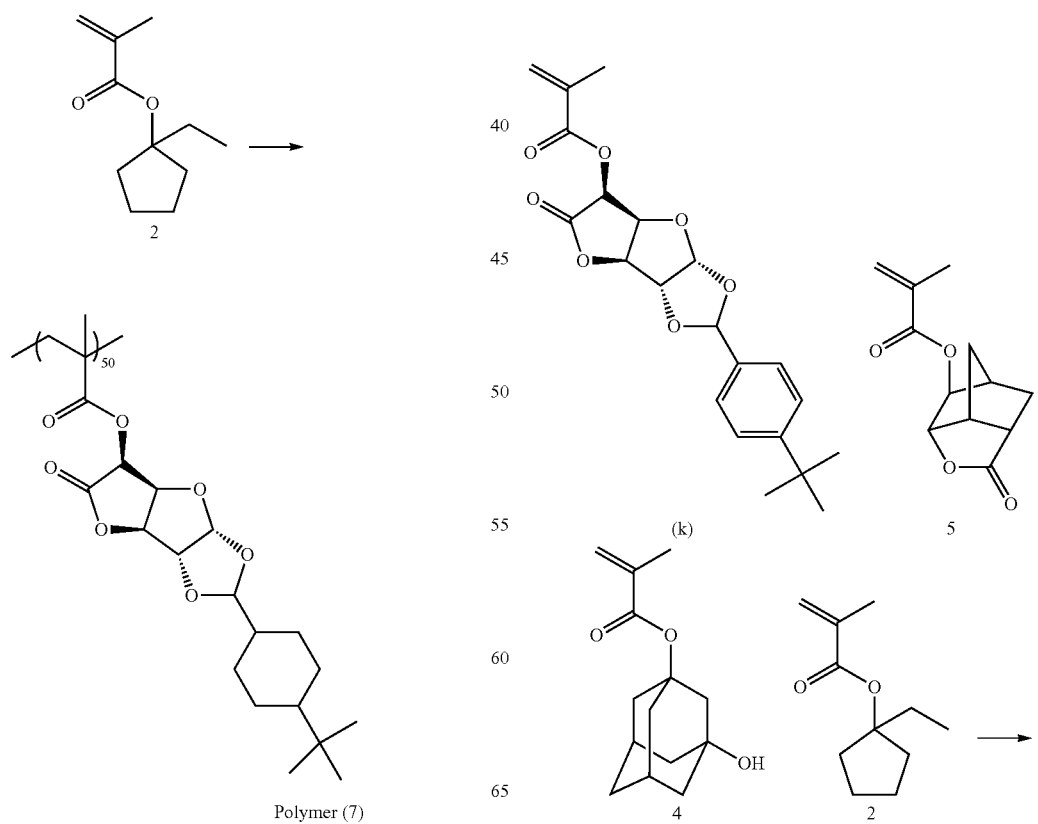

-continued

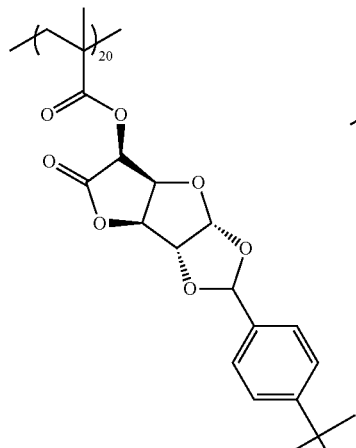

Polymer (8)

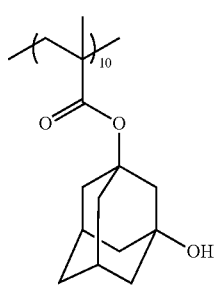

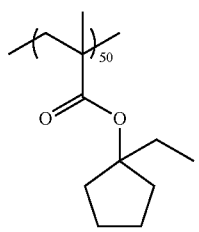

A three-necked flask was charged with 94.0 g of cyclohexanone in a nitrogen atmosphere and heated at 65° C. A solution having 15.5 g of Compound (k), 8.9 g of Compound (5), 4.7 g of Compound (4), 18.2 g of Compound (2) and a polymerization initiator V-65 (manufactured by Wako Pure Chemical Industries, Ltd.) in an amount of 1.5% by mole relative to the monomers dissolved in 174.5 g of cyclohexanone was added dropwise thereto over 6 hours. After completion of the dropwise addition, the mixture was allowed to react at 65° C. for an additional 2 hours. The reaction solution was allowed to stand for cooling and then added dropwise to a mixed solution of 1,700 g of heptane and 700 g of ethyl acetate over 20 minutes; and a deposited powder was collected by filtration and dried to obtain 38.6 g of Polymer (8).

The resulting Polymer (8) had a weight average molecular of 9,800 as reduced into standard polystyrene by the GPC method and a degree of dispersion (Mw/Mn) of 1.58.

Example 15

Synthesis of Polymer (9)

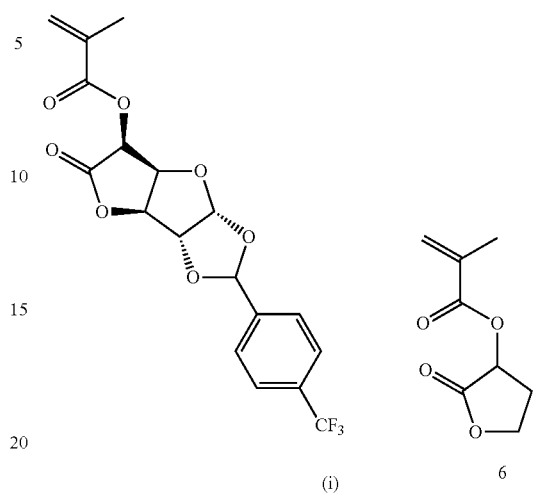

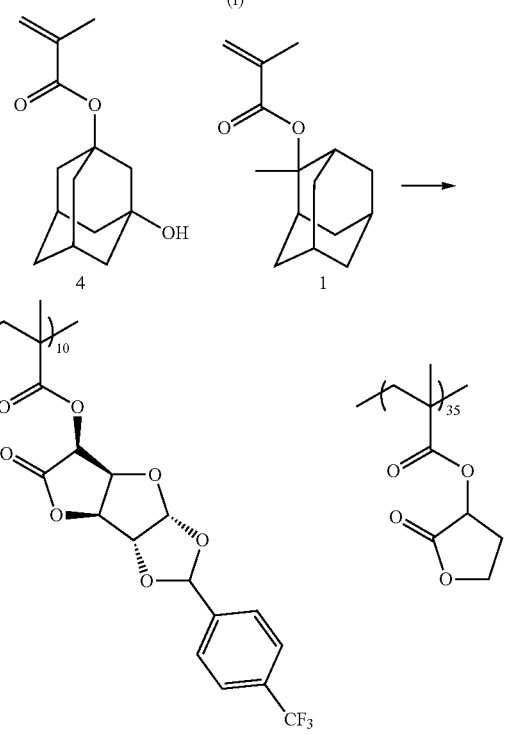

Polymer (9)

A three-necked flask was charged with 48.0 g of cyclohexanone in a nitrogen atmosphere and heated at 80° C. A solution having 8.0 g of Compound (i), 11.9 g of Compound (6), 7.9 g of Compound (4), 18.8 g of Compound (1) and a polymerization initiator V-601 (manufactured by Wako Pure Chemical Industries, Ltd.) in an amount of 3% by mole relative to the monomers dissolved in 89.2 g of cyclohexanone was added dropwise thereto over 6 hours. After completion of the dropwise addition, the mixture was allowed to react at 80° C. for an additional 2 hours. The reaction solution was allowed to stand for cooling and then added dropwise to a mixed solution of 1,400 g of heptane and 600 g of ethyl acetate over 20 minutes; and a deposited powder was collected by filtration and dried to obtain 38.5 g of Polymer (9).

The resulting Polymer (9) had a weight average molecular of 13,200 as reduced into standard polystyrene by the GPC method and a degree of dispersion (Mw/Mn) of 1.66.

Example 16

A solution of 2 g of the above-obtained Polymer (7), 80 mg of triphenyl sulfonium pentafluorobenzene sulfonate, 7 mg of tri-n-octylamine and 4 mg of MEGAFAC F176 (manufactured by DIC Corporation) was prepared using a mixed solvent of propylene glycol monomethyl ether acetate and propylene glycol monomethyl ether (6/4) (mass ratio) so as to have a solid concentration of 5% by mass and filtered through a polyethylene filter having a pore size of 0.1 μm, thereby obtaining a positive working resist composition.

On the other hand, an antireflection film DUV-42, manufactured by Brewer Science, Inc. was uniformly coated in a thickness of 600 angstroms on a silicon substrate which had been treated with hexamethylsilazane by a spin coater, dried on a hot plate at 100° C. for 90 seconds and then heated for drying at 190° C. for 240 seconds. Thereafter, the foregoing positive working resist composition was coated by a spin coater and dried at 110° C. for 90 seconds, thereby forming a resist film having a thickness of 180 nm. This resist film was exposed through a mask by an ArF excimer laser stepper (manufactured by ASML, NA=0.75, ⅔ zonal illumination), and immediately after the exposure, the resist film was heated on a hot plate at 120° C. for 90 seconds. Furthermore, the resulting resist film was developed with a 2.38% by mass tetramethylammonium hydroxide aqueous solution at 23° C. for 60 seconds, rinsed with pure water for 30 seconds and then dried to obtain a pattern of 100-nm line-and-space 1/1.

Also, each of the above-obtained Polymers (2), (3), (5), (8) and (9) was used in place of Polymer (7) to obtain a pattern in the same manner.

According to the invention, a novel polymerizable compound and a novel polymer compound obtained by using the same can be provided, and this polymer compound is especially useful for the formation of a pattern in the semiconductor field.

The entire disclosure of Japanese Patent Application No. 2008-317753 filed on Dec. 12, 2008, from which the benefit of foreign priority has been claimed in the present application, is incorporated herein by reference, as if fully set forth.

What is claimed is:

1. A polymerizable compound represented by the following general formula (cb-1):

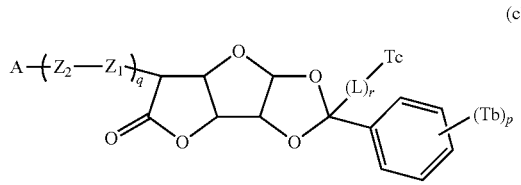

(cb-1)

wherein

A represents an optionally substituted methacryl group, an optionally substituted acryl group or an optionally substituted norbornene group;

each $Z_1$ independently represents a single bond, an ether bond, an ester bond, an amide bond, a urethane bond or a urea bond;

each $Z_2$ independently represents a single bond or an optionally substituted chain or cyclic alkylene group;

each Tb independently represents a halogen atom, an optionally substituted alkyl group, an optionally substituted cycloalkyl group, an optionally substituted alkoxy group, an optionally substituted acyl group, an optionally substituted alkyloxycarbonyl group, a carboxy group, a nitrile group, a hydroxyl group, an optionally substituted amide group or an optionally substituted aryl group; and when plural Tbs are present, Tbs may be bonded to each other to form a fused ring, which may contain a hetero atom, together with the benzene ring on which Tb is substituted;

Tc represents a hydrogen atom, a halogen atom, an optionally substituted alkyl group, an optionally substituted cycloalkyl group, a nitrile group, a hydroxyl group, an optionally substituted amide group or an optionally substituted aryl group;

each L independently represents a carbonyl group, a carbonyloxy group or an ether bond;

p represents an integer of from 0 to 5;

q represents an integer of from 0 to 5; and r represents an integer of from 0 to 5.

2. The polymerizable compound according to claim 1, which is represented by the following general formula (cb-2):

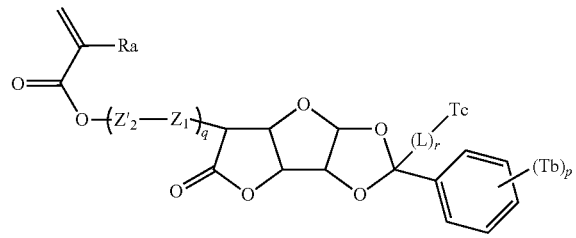

(cb-2)

wherein

Ra represents a hydrogen atom, a fluorine atom, a methyl group a trifluoromethyl group;

each $Z_1$ independently represents a single bond, an ether bond, an ester bond, an amide bond, a urethane bond or a urea bond;

each $Z_2'$ independently represents an optionally substituted chain or cyclic alkylene group;

each Tb independently represents a halogen atom, an optionally substituted alkyl group, an optionally substituted cycloalkyl group, an optionally substituted alkoxy group, an optionally substituted acyl group, an optionally substituted alkyloxycarbonyl group, a carboxy group, a nitrile group, a hydroxyl group, an optionally substituted amide group or an optionally substituted aryl group; and when plural Tbs are present, Tbs may be bonded to each other to form a fused ring, which may contain a hetero atom, together with the benzene ring on which Tb is substituted;

Tc represents a hydrogen atom, a halogen atom, an optionally substituted alkyl group, an optionally substituted cycloalkyl group, a nitrile group, a hydroxyl group, an optionally substituted amide group or an optionally substituted aryl group;

each L independently represents a carbonyl group, a carbonyloxy group or an ether bond;

p represents an integer of from 0 to 5;

q represents an integer of from 0 to 5; and r represents an integer of from 0 to 5.

3. The polymerizable compound according to claim 1, which is represented by the following general formula (cb-3):

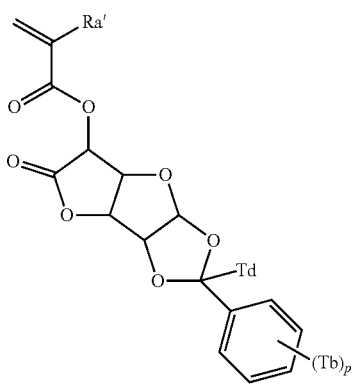

(cb-3)

wherein

Ra' represents a hydrogen atom or a methyl group;

each Tb independently represents a halogen atom, an optionally substituted alkyl group, an optionally substituted cycloalkyl group, an optionally substituted alkoxy group, an optionally substituted acyl group, an optionally substituted alkyloxycarbonyl group, a carboxy group, a nitrile group, a hydroxyl group, an optionally substituted amide group or an optionally substituted aryl group; and when plural Tbs are present, Tbs may be bonded to each other to form a fused ring, which may contain a hetero atom, together with the benzene ring on which Tb is substituted;

Td represents a hydrogen atom or a methyl group; and p represents an integer of from 0 to 5.

4. The polymerizable compound according to claim 1, wherein q is 0 or 1.

5. The polymerizable compound according to claim 1, wherein r is 0 or 1.

6. The polymerizable compound according to claim 1, wherein $Z_1$ represents an ether bond or an ester bond.

7. The polymerizable compound according to claim 1, wherein $Z_2$ represents an optionally substituted chain alkylene group.

8. A polymer compound obtained by polymerizing the polymerizable compound according to claim 1.

* * * * *